United States Patent
Chappelow et al.

(10) Patent No.: US 6,610,759 B1
(45) Date of Patent: Aug. 26, 2003

(54) CATIONICALLY POLYMERIZABLE ADHESIVE COMPOSITION CONTAINING AN ACIDIC COMPONENT AND METHODS AND MATERIALS EMPLOYING SAME

(75) Inventors: Cecil C. Chappelow, Leawood, KS (US); Charles S. Pinzino, Kansas City, MO (US); J. David Eick, Gladstone, MO (US); James Code, Kansas City, MO (US); Joel D. Oxman, St. Louis Park, MN (US); Sharon M. Rozzi, Stillwater, MN (US)

(73) Assignees: Curators of the University of Missouri, Columbia, MO (US); 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/519,532

(22) Filed: Mar. 6, 2000

(51) Int. Cl.⁷ .............................. C08F 2/48; C08F 2/50; C08K 5/09; C08K 5/20
(52) U.S. Cl. .............................. 522/25; 522/14; 522/15; 522/31; 522/100; 522/148; 522/908; 522/162; 522/169; 522/168; 522/170; 522/182; 522/183; 523/109; 523/115; 523/116; 523/118; 523/300; 424/49; 424/52; 424/53; 424/56; 427/508; 427/516; 427/517
(58) Field of Search .............................. 522/14, 15, 25, 522/31, 100, 148, 908, 162, 169, 168, 170, 182, 183; 523/109, 115, 116, 118, 300; 424/49, 52, 53, 56; 427/508, 516, 517

(56) References Cited

U.S. PATENT DOCUMENTS

| | | |
|---|---|---|
| 4,308,118 A | 12/1981 | Dudgeon |
| 4,368,314 A | 1/1983 | Endo et al. |
| 4,387,215 A | 6/1983 | Bailey |
| 4,528,386 A | 7/1985 | Poshkus |
| 4,656,294 A | 4/1987 | Kanayawa |
| 4,719,149 A | 1/1988 | Aasen et al. |
| 4,738,899 A | 4/1988 | Bluestein et al. |
| 4,851,550 A | 7/1989 | Mues et al. |
| 4,855,367 A | 8/1989 | Flury et al. |
| 4,870,193 A | 9/1989 | Taguchi et al. |
| 4,876,323 A | 10/1989 | Engel et al. |
| 4,988,607 A | 1/1991 | Ali |
| 5,194,365 A | 3/1993 | Goodin et al. |
| 5,236,812 A | 8/1993 | Vassiliou et al. |
| 5,276,068 A | 1/1994 | Waknine ............ 522/28 |
| 5,298,631 A | 3/1994 | Sanda et al. |
| 5,362,889 A | 11/1994 | Stansbury |
| 5,463,008 A | 10/1995 | Stansbury |
| 5,492,942 A | 2/1996 | Kobayashi et al. |
| 5,556,896 A | 9/1996 | Byerley et al. |
| 5,631,307 A | 5/1997 | Tanaka et al. |
| 5,798,396 A | 8/1998 | Takahashi et al. |
| 5,808,108 A | 9/1998 | Chappelow et al. |
| 5,877,232 A | 3/1999 | Storch et al. |
| 5,980,253 A | 11/1999 | Oxman et al. |
| 5,998,495 A | 12/1999 | Oxman et al. |
| 6,025,406 A | 2/2000 | Oxman et al. |
| 6,126,922 A | * 10/2000 | Rozzi et al. ............ 424/49 |

FOREIGN PATENT DOCUMENTS

| | | |
|---|---|---|
| EP | WO 96/13538 | 5/1996 |
| EP | WO 97/18792 | 5/1997 |
| EP | WO 98/46197 | 10/1998 |
| EP | WO 98/47046 | 10/1998 |
| EP | WO 98/47047 | 10/1998 |
| JP | 64726 | 4/1986 |
| WO | WO 99/34766 | 7/1999 |

OTHER PUBLICATIONS

Anderson et al., *Silicon Compounds: Register and Review*, 5th Edition, Piscataway, N.J., p. 4.
Bailey, "Matrices that Expand on Curing for High Strength Composites and Adhesives," *Materials Science & Engineering*, A126, pp. 271–279, 1990.
Bailey et al., "Radical Ring–Opening Polymerization and Copolymerization with Expansion in Volume," *Journal of Polymer Science: Polymer Symposium*, vol. 64, pp. 17–26, 1978.
Blomquist et al., "The Mineral Acid–catalyzed Reaction of Cyclohexene with Formaldehyde," *Acid–Catalyzed Reaction of Cyclohexene with Formaldehyde*, pp. 6025–6030, Nov. 20, 1957.
Byerley et al., "Expandable Matrix Monomers for Dental Composites," *Journal of Dental Research*, 69(SI), p. 263, Abstract No. 1233, Mar. 1990.
Byerley et al., "Expandable Matrix Monomers for Dental Composites," pp. 1–9, Mar., 1990.
Byerley et al., "Spiroorthocarbonates: Polymerization and Volume Change Determinations," *Journal of Dental Research*, 70(SI), p. 527, Abstract No. 2087, 1991.
DeWolf, "Synthesis of Carboxylic and Carbonic Ortho Esters," pp. 153–172, Mar. 1974.
He et al., "Study of Copolymer Epoxy Resin Matrix without Shrinkage: Part 1 Volume Change During Cure Processes," *Chinese Journal of Polymer Science*, vol. 6, pp. 30–35, 1988.

(List continued on next page.)

Primary Examiner—James J. Seidleck
Assistant Examiner—Sanza L McClendon
(74) Attorney, Agent, or Firm—Stinson Morrison Hecker LLP

(57) ABSTRACT

An adhesive composition that includes a mixture of a cationically polymerizable component, an acidic component, and an initiator is provided. Preferably, the initiator comprises an iodonium salt, a visible light sensitizer, and an electron donor compound, wherein the initiator has a photoinduced potential greater than or equal to that of N,N-dimethylaniline in a standard solution of $2.9 \times 10^{-5}$ moles/g diphenyl iodonium hexafluoroantimonate and $1.5 \times 10^{-5}$ moles/g camphorquinone in 2-butanone. This adhesive composition is cationically polymerizable and is able to bond to hard tissue and cationic restorative materials upon curing.

43 Claims, No Drawings

OTHER PUBLICATIONS

He et al., "Epoxy Resin Copolymer with Zero Shrinkage, Part I vol. Change on Cure," *Journal of Material Science,* vol. 24, pp. 1528–1532, 1989.

He et al., "Epoxy Resin Copolymer with Zero Shrinkage, Part II Thermal and Mechanical Properties," *Journal of Material Science,* vol. 26, pp. 3792–3796, 1991.

He et al., *Chem. Abs.,* 109, Ab. #74464, 1989.

Manzhen, "Photoinitiated Cationic Copolymerization of an Alicyclic Epoxy Compound and a Spiroorthocarbonate," *International Journal of Polymeric Materials,* vol. 18, pp. 1–7, 1992.

Manzhen, "Effect of Structural Difference of Photoinitiator on Photocopolymerization of an Alicyclic Epoxy Compound and a Spiroorthocarbonate," *International Journal of Polymeric Materials,* vol. 18, pp. 189–195, 1992.

Millich et al., "Expansion Polymerization Density Change Determination," pp. 1–17.

Phillips, "Restorative Resins," *Science of Dental Materials,* 9th ed., pp. 215–233, 1991.

Stansbury et al., "Evaluation of Spiro Orthocarbonate Monomers Capable of Polymerization with Expansion as Ingredients in Dental Composite Materials", *Progress in Biomedical Polymers,* pp. 133–139, 1990.

Anderson et al., "A Simple Procedure for the Epoxidation of Acid–Sensitive Olefinic Compounds with m–Chloroperbenzoic Acid in an Alkaline Biphasic Solvent System," *Journal of Organic Chemistry,* vol. 38, pp. 2267–2268, 1973.

Bai et al., "Gaodeng Zueziao Huazue Zuebao", vol. 16, Abstract No. 123:258384, pp. 1487–1489, 1995.

Bailey et al., "Convenient Preparation of Trans–1,3–Dioxadecalin Via the Prins Reaction," *Synthetic Communications,* 17(15), pp. 1769–1772, 1987.

Bailey et al., "Recent Advances in Ionic Polymerization with Expansion in Volume," *Polymers Preprint,* vol. 26, pp. 50–51, 1985.

Brautigam et al., "New Vinyl Ether Oligomers and Diluent Monomers for Cationic Curing," *Vectomer™ 005R Vinyl Ether Oligomers and Monomers,* 6 pages, 1990.

Byerley et al., "Synthesis and Polymerization of New Expanding Dental Monomers," *Dental Materials,* vol. 8, pp. 345–350, Nov. 1992.

Chappell et al., "Density Determination and Volume Change Calculations for Monomer to Polymer," *Journal of Dental Research,* 75(SI), p. 462, Abstract No. 492, 1995.

Chappelow et al., "Design and Development of Isocyanatoacrylates as Dental Adhesives," *Journal of Dental Research,* 75(2), pp. 761–767, 1996.

Chappelow et al., "Development of Non–shrinking adhesive Composite Materials," Presented at the Dental Materials Symposium on Progress in–Dentin, Dentin Bonding, and Restorative Materials at the 27th Annual Meeting of the American Association for Dental Research, Minneapolis, Minnesota, Mar. 1998.

Chappelow et al., "Isocyanatoacrylate Copolymer Dental Adhesives—Priming and Crosslinking Systems," *Academy of Dental Materials,* vol. 9, p. 255, 1996.

Chappelow et al., "Photocured Epoxy/SOC Matrix Resin Systems for Dental Composites," *Polymer Preprints,* 38(2), p. 90, 1997.

Chappelow et al., "Photopolymerization of Epoxy/Polyol Mixtures Containing Spiroorthocarbonates," *Journal of Dental Research,* 76(SI), p. 40, 1997.

Chappelow et al., "Photoreactivity of Expanding Monomers in Dental Matrix Resins Systems," *Journal of Dental Research,* 77B, p. 639, Abstract No. 62, Jun. 24, 1998.

Chappelow et al., "Photoreactivity of Substituted 1,5,7,11–Tetraoxaspiro[5,5]undecane/Diepoxide/Poplyol Matrix Resin Systems," Presented at the 27th Annual Meeting of the American Association for Dental Research, Minneapolis, Minnesota, Mar. 1998.

Chappelow et al., "Synthesis and Photopolymerization of Substituted 1,5,7,11–Tetraoxaspiro[5,5]undecanes," *Journal of Dental Research,* 75(SI), p. 235, Abstract No. 492, 1995.

Cipollina et al., "Synthesis and Biological Activity of the Putative Metabolites of the Atypical Antipsychotic Agent Tiospirone," *Journal of Medical Chemistry,* vol. 34, pp. 3316–3328, 1991.

Corey et al., "A Mild Procedure for the Conversion of 1,2–Diols to Olefins," *Tetrahedron Letters,* vol. 23, pp. 1979–1982, 1982.

Delmas, et al., "Selective Synthesis of 4–Aryl–1,3–cioxanes from Arylalkenes and Paraformaldehyde using an Ion Exchange Resin as Catalyst; Extension to Natural Compounds," *A Communication to Synthesis,* 0039–7881/80–1132–0871, pp. 871–872, 1980.

Delmas, et al., "Supported Acid Catalysis with Ion–Exchange Resins I. Role of Benzene as Solvent During the Prins Reaction," *Journal of Molecular Catalysis,* 4(1978), pp. 443–447, 1978.

Depres et al., "Improved Selectivity in the Preparation of Some 1,1–Difunctionalized 3–Cyclopentenes. High Yield Synthesis of 3–Cyclopentenecarboxylic Acid," *Journal of Organic Chemistry,* vol. 49, pp. 928–931, 1984.

Dougherty et al., "Vinyl Ethers for Cationic UV Curing," RADCURE '86 Conf. Proc. 10th, *Assoc. Finish Processes SME,* pp. 1–8, 1986.

Eick et al., "Photoreactivity of Vinyl Ether/Epoxy–Based Candidate Dental Adhesives," *Journal of Dental Research,* 77B, p. 639, Abstract 63, Jun. 24, 1998.

Eick et al., "Adhesives and Nonshrinking Dental Resins of the Future," *Journal of Dental Research,* 72(SI), p. 189, Abstract No. 685, 1993.

Eick et al., "Properties of Expanding SOC/Epoxy Copolymers for Dental Use," *Journal of Dental Research,* 71(SI), p. 598, Abstract No. 662, 1992.

Eick et al., "Properties of expanding SOC/epoxy Copolymers for Dental Use in Dental Composites," *Dental Material,* vol. 9, pp. 123–127, Mar. 1993.

Eick et al., "Symposium: Dental Composites and Adhesives in the 21st Century—The Gunnar Ryge Memorial Symposium," *Journal of Dental Research,* 72(SI), p. 189, Abstract No. 682, 1993.

Endo et al., "Polymerization and Block Copolymerization Initiated by Unusually Stable Living Propagating Species Formed in the Cationic Polymerization of Spiro Ortho Carbonate," vol. 21, pp. 1186–1187, 1988.

Endo et al., "Synthesis and Cationic Polymerization of 3,9–Dibenzyl–1,5,7,11–tetraoxaspiro[5,5]undecane," *Macromolecules,* vol. 20, pp. 1416–1419, 1987.

Fujinami et al., "Effect of Substituents on Cationic Polymerization of Six–Membered Spiro Orthocarbonates," *Polymer Journal,* vol. 9, pp. 553–560, 1977.

Gharbi et al., "Condensation of Substituted Styrenes with Aliphatic and Aromatic Aldehydes; An Extension of the Prins Reaction," *A Communication to Synthesis*, 0039–7881/81/0532–0361, pp. 361–362, 1981.

Harris et al., "Hompolymerization of Spiroorthocarbonate: A Computational Study," *Journal of Dental Research*, 77(SI), p. 154, 1998.

Hellier et al., "Carbon–13 N.M.R. Studies of Stereoisomerism in a Spiro Carbonate," *Journal of Chemical Research*, (S), pp. 1388–1399, 1988.

Heslinga, "The Acetolysis of 4–Phenyl–1,3–Diozan. A New Synthesis of Cinnamyl Esters," *Recueil*, vol. 78, pp. 473–479, 1959; CA 54, 1403e, *Rec. Travl. Chim.*

Janzen et al., "Synthesis and Spin–Trapping Chemistry of 5,5–Dimethyl–2–(trifluoromethyl)–1–pyrroline N–Oxide," *Journal of Organic Chemistry*, vol. 60, pp. 5434–5440, 1995.

Kostoryz et al., "Reduced Cytotoxicity of New Dental Resins Containing Spiroorthocarbonate/Epoxy Copolymers," *Journal of Dental Research*, 76(SI), p. 321, 1997.

Krapcho et al., "2–Carbethoxyclyclooctanone," *Organic Synthesis*, vol. 47, pp. 20–23, 1967.

March, "Aliphatic Nucleophilic Substitution," *Advanced Organic Chemistry*, 4th Ed., pp. 392–393, 1992.

May, "Photopolylmerization Test Procedure—Visible Light photolysis using Photo–DSC Technique," *Epoxy Resins Chemistry and Technology*, 1988.

Millich et al., "Determination of Density Changes with Expansion Polymerization," *Journal of Polymer Science: Part B: Polymer Physics*, vol. 31, pp. 729–733, 1993.

Penny et al., "Phenyl Phosphorodichloridate in the Synthesis of Cyclic Phosphate Diesters of Biological Interest," *Canadian Journal of Chemistry*, vol. 56, pp. 2396–2404, 1978.

Pinzino et al., "Visible Light Inducted Polymerization Studies of SOCs and Monofunctional Epoxides," *Journal of Dental Research*, 76(SI), p. 41, 1997.

Power et al., "Photoinitiated Polymerization of Isocyanatoacrylates as Dental Adhesives," *Journal of Dental Research*, 76(SI), p. 257, 1997.

Power et al., Visible Light Cured Isocyanatoacrylate Base Dental Adhesives, *Polymer Preprints*, 38(2), p. 145, 1997.

Rose et al., "A Study of the Mutagenicity of Non–Shrinking Spiroorthocarbonate Co–Polymers," *Journal of Dental Research*, 75(SI), p. 329, Abstract No. 2492, 1996.

Sadhir et al., Expanding Monomers Synthesis, Characterization, and Applications, *CRC Press*, 1992; pp. 329–332.

Sakai et al., "Reaction of Dialkyltin Dialkoxides with Carbon Disulfide at Higher Temperature. Preparation of Orthocarbonates," *Journal of Organic Chemistry*, vol. 36, pp. 1176–1180, 1971.

Soai et al., "A Chemoselective One–Step Reduction of β–Ketoesters to 1,3–Diols," *Syntheses Communications*, pp. 605–607, 1984.

Stansbury et al., "Evaluation of Spiro Orthocarbonate Monomers Capable of Polymerization with Expansion as Ingredients in Dental Composite Materials," *Polymeric Material Science and Engineering*, vol. 59, pp. 402–406, 1988.

Stansbury, "Improved Monomers for Double Ring Opening Polymerization with Expansion," *Journal of Dental Research*, vol. 70, p. 527, Abstract No. 2088, 1991.

Thompson et al., Dental Resins with Reduced Shrinkage During Hardening, *Journal of Dental Research*, vol. 58, pp. 1522–1532, 1979.

Uchida et al., "The Prins Reaction of Cyclooctene and Cyclododecene," *Bulletin of the Chemical Society of Japan*, vol. 46, pp. 2512–2515, 1973.

Yano et al., "Activation and Control of the Reaction of Dioxastannolane with Carbon Disulfide and Phenyl Isothiocyanate by the Addition of Bases," *Chem. Ber.*, vol. 124, pp. 1881–1884, 1991.

Yourtee et al., "The Effect of Spiroorthocarbonate Volume Modifier Co–monomers on the In Vitro Toxicology of Trial Non–shrinking Dental Epoxy Co–polymers," *Research Communications in Molecular Pathology and Pharmacology*, vol. 86, pp. 347–360, Dec. 1994.

Zhuang et al., "Evaluation of Tetrazolium Colorimetric Test for Biomaterial Cytotoxicity Determination," *Journal of Dental Research*, 72(SI), p. 162, Abstract No. 469, 1993.

BASF, Vinyl Ethers, The Innovative Challenge Brochure, 2 pages, no date indicated.

Allied Signal Inc., Vectomer™ 2010 Brochure, 1 page, 1990.

Allied Signal Inc., Vectomer™ 2015 Brochure, 1 page, 1990.

Allied Signal Inc., Vectomer™ 2020 Brochure, 1 page, 1990.

Allied Signal Inc., Vectomer™ 4010 Brochure, 1 page, 1990.

Allied Signal Inc., Vectomer™ 4020 Brochure, 1 page, 1990.

"Rapi–Cure—Vinyl Ethers Reactivity Agents for Radiation Curing Systems," *International Specialty Products*, 21 pages, no date indicated.

* cited by examiner

CATIONICALLY POLYMERIZABLE ADHESIVE COMPOSITION CONTAINING AN ACIDIC COMPONENT AND METHODS AND MATERIALS EMPLOYING SAME

STATEMENT REGARDING FEDERALLY SPONSORED RESEARCH OR DEVELOPMENT

The government has certain rights in this invention. This invention was developed under federal funding from the National Institute of Dental Research, Grant No. 5 PO1 DEO9696-09.

CROSS-REFERENCE TO RELATED APPLICATIONS

Not applicable.

FIELD OF THE INVENTION

This invention relates in general to compositions of matter and, more particularly, to polymerizable adhesive compositions that include a cationically polymerizable component, an acidic component, and an initiator capable of initiating cationic polymerization. These compositions may also include a polyol and/or a free radically polymerizable component. The polymerizable compositions of the present invention are useful for a variety of applications, including use as adhesives for bonding to hard tissue and cationically curable or cured restorative materials.

BACKGROUND OF THE INTVENTION

Dental compositions such as composites, sealants, and cements generally will not bond sufficiently to tooth enamel or dentin unless the enamel or dentin is pretreated with an adhesive layer, etchant, and/or primer. Typically, the tooth is etched with an acidic solution, and optionally, this is followed by application of a (meth)acrylate-based pre-adhesive composition that is polymerized using a redox, chemically or photochemically activated free radical initiator to form a layer of adhesive. The dental composition, which is typically a filled (meth)acrylate-based composition, is then placed over the adhesive and polymerized using a free radical initiator system to form a hard, wear-resistant material. The adhesive, therefore, bonds to both the acid-etched tooth and to the dental composition.

(Meth)acrylate-based dental compositions exhibit a relatively high degree of volumetric shrinkage upon polymerization. Accordingly, cationically curable compositions, and hybrid compositions featuring both cationically and free radically curable components, have been suggested as alternatives. Such compositions, which typically include epoxy resins as the cationically curable component, exhibit less shrinkage upon cure than compositions that are made predominately of (meth)acrylate. If such cationically curable components are to be used, the pre-adhesive used to bond such components may contain a substantial number of cationically curable TID groups. However, pre-adhesive compositions containing relatively large amounts of cationically curable groups that have previously been disclosed do not bond well to hard tissues, such as tooth enamel and dentin, because the hard tissue inhibits polymerization of such materials.

An epoxide/polyol polymeric composition that includes a photoinitiator system comprising an iodonium salt, a visible light sensitizer, and an electron donor compound is disclosed by one of the present inventors, with another, in U.S. Pat. No. 5,998,495 (the '495 patent). The '495 patent further suggests that other cationically polymerizable polymers can be incorporated into the epoxide/polyol polymeric composition. U.S. Pat. No. 6,025,406 (the '406 patent) discloses an epoxide polymeric composition that includes a photoinitiator system comprising an iodonium salt, a visible light sensitizer, and an electron donor compound.

U.S. Pat. No. 5,980,253 discloses treating hard tissues by applying a composition that includes a cationically active functional group, a free radically active functional group, and a polymerization initiator capable of initiating free radical polymerization. However, the disclosure specifies that the amount of cationically active functional group present is no greater than about 0.0075 moles per gram of composition.

PCT Application No. PCT/US97/08534 discloses dental compositions comprising a polymerizable component, an acid reactive filler, a hydrophilic component, a polymerization initiator, and an acid. PCT Application No. PCT/US96/16299 discloses dental compositions comprising a polymerizable component, a fluoride-releasing material, a hydrophilic component, a polymerization initiator, and an acid.

Despite the advances resulting from the above-noted polymeric compositions, a need still exists for cationically polymerizable compositions having adhesive properties to hard tissues. Still further, these adhesive compositions should be able to successfully polymerize on the surface of hard tissue to form a strong bond with the hard tissue, yet at the same time, they should successfully bond to subsequently applied compositions that include cationically active groups.

SUMMARY OF THE INVENTION

The present invention is directed to an adhesive composition that includes a mixture of a cationically polymerizable component, an acidic component, and an initiator capable of initiating cationic polymerization. Preferably, the initiator comprises an iodonium salt, a visible light sensitizer, and an electron donor compound, wherein the initiator has a photoinduced potential greater than or equal to that of N,N-dimethylaniline in a standard solution of $2.9 \times 10^{-5}$ moles/g diphenyl iodoniun hexafluoroantimonate and $1.5 \times 10^{-5}$ moles/g camphorquinone in 2-butanone. This adhesive composition is cationically polymerizable and is able to bond to hard tissue and cationically curable or cured restorative materials.

Additional novel features and advantages of the invention will be set forth in part in the description which follows, and in part will become apparent to those skilled in the art upon examination of the following, or may be learned from the practice of the invention. The objects and advantages of the invention may be realized and attained by means of the compositions particularly pointed out in the appended claims.

DETAILED DESCRIPTION OF THE PREFERRED EMBODIMENT

The present invention is directed to an adhesive composition comprising a cationically polymerizable component, an acidic component, and an initiator capable of initiating cationic polymerization. These components are mixed to form the adhesive composition. These components may be sold unmixed so that the composition can be made just prior to use. The composition results in a polymerized product when one or more of the cationically polymerizable components in the composition are contacted with the initiator under conditions sufficient to promote polymerization of the component. This adhesive composition may also include a compound having a reactive olefinic moiety (an unsaturated aliphatic hydrocarbon functional group), a free radically polymerizable component, a polyol, or combinations thereof.

Any cationically polymerizable component or combinations thereof may be used in the adhesive composition of the present invention. As used herein, a "cationically polymerizable component" refers to a compound having a cationically active functional group. This cationically active functional group is a chemical moiety that is activated in the presence of an initiator capable of initiating cationic polymerization such that it is available for reaction with other compounds bearing cationically active functional groups. Examples of cationically polymerizable components include, but are not limited to, epoxy resins, vinyl ethers, oxetanes, spiroothrocarbonates, spiroorthoesters, and combinations thereof. Spiroorthocarbonates are esters of orthocarboxylic acid and have four oxygen atoms bonded to a single carbon atom, with the carbon atom being common to two ring systems.

Epoxy resins have an oxirane ring, which is polymerizable by ring opening. Epoxy resins include monomeric epoxy compounds and epoxides of the polymeric type and can be aliphatic, cycloaliphatic, aromatic or heterocyclic. Epoxy resins generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymershaving pendent epoxy groups (e.g., a glycidyl (meth)acrylate polymer or copolymer). The epoxides may be provided by one compound or may be mixtures of compounds containing one, two, or more epoxy groups per molecule. The average number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. For example, the backbone may be of any type and substituent groups thereon can be any group that does not substantially interfere with cationic polymerization at room temperature. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexene oxide groups such as epoxycyclohexanecarboxylates, typified by 3,4-epoxycyclohexylmethyl-3,4 epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl)adipate. For a more detailed list of useful epoxides of this nature, reference is made to the U.S. Pat. No. 3,117,099.

Further epoxy-containing materials which are useful in the compositions of this invention include glycidyl ether monomers. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane). Further examples of epoxides of this type are described in U.S. Pat. No. 3,018,262, and in Handbook of Epoxy Resins by Lee and Neville, McGrawv-Hill Book Co., New York (1967).

There are a host of commercially available epoxy resins which can be used in this invention. In particular, epoxides which are readily available include octadecylene oxide, epichlorohydrin, styrene oxide, vinyl cyclohexene oxide, glycidol, glycidylmethacrylate, diglycidyl ether of Bisphendl A (e.g., those available under the trade designations Epon 828™, Epon 825™. Epon 1004™ and Epon 1010™ from Shell Chemical Co., and DER-333™, DER-332™, and DER-334™, from Dow Chemical Co.), vinylcyclohexene dioxide (e.g., ERL-4206™ from Union Carbide Corp.), 3,4-epoxycyclohexylmethyl-3,4-epoxycyclohexene carboxylate (e.g., ERL-4221™ or CYRACURE UVR 6110™ or UVR 6105™ from Union Carbide Corp.), 3,4-epoxy-6-methylcyclohexylmethyl-3,4-epoxy-6-methyl-cyclohexene carboxylate (e.g., ERL-420™ from Union Carbide Corp.), bis(3,4-epoxy-6-methylcyclohexylmethyl)adipate (e.g., ERL-4289™ from Union Carbide Corp.), bis(2,3-epoxycyclopentyl)ether (e.g., ERL-0400™ from Union Carbide Corp.), aliphatic epoxy modified from polypropylene glycol (e.g., ERL-4050™ and ERL-4052™ from Union Carbide Corp.), dipentene dioxide (e.g., ERL-4269™ from Union Carbide Corp.), epoxidized polybutadiene (e.g., Oxiron 2001™ from FMC Corp.), silicone resin containing epoxy functionality, flamne retardant epoxy resins (e.g., DER-580™, a brominated bisphenol type epoxy resin available from Dow Chemical Co.), 1,4-butanediol diglycidyl ether of phenolformaldehyde novolak (e.g., DEN-431™ and DEN-438™ from Dow Chemical Co.), resorcinol diglycidyl ether (e.g., Kopoxite™ from Koppers Company, Inc.), bis(3,4-epoxycyclohexyl)adipate (e.g., ERL-4299™ or TVR-6128™, from Union Carbide Corp.), 2-(3,4-epoxycyclohexyl-5,5-spiro-3,4-epoxy) cyclohexane-metadioxane (e.g., ERL-4234™ from Union Carbide Corp.), vinylcyclohexene monoxide 1,2-epoxyhexadecane (e.g, UVR-6216™ from Union Carbide Corp.), alkyl glycidyl ethers such as alkyl $C_8$–$C_{10}$ glycidyl ether (e.g., HELOXY Modifier 7™ from Shell Chemical Co.), alkyl $C_{12}$–$C_{14}$ glycidyl ether (e.g., HELOXY Modifier 8™ from Shell Chemical Co.), butyl glycidyl ether (e.g., HELOXY Modifier 61™ from Shell Chemical Co.), cresyl glycidyl ether (e.g., HELOXY Modifier 62™ from Shell Chemical Co.), p-terbutylphenyl glycidyl ether (e.g., HELOXY Modifier 65™ from Shell Chemical Co.), polyfunctional glycidyl ethers such as diglycidyl ether of 1,4-butanedol (e.g., HELOXY Modifier 67™ from Shell Chemical Co.), diglycidyl ether of neopentyl glycol (e.g., HELOXY Modifier 68™ from Shell Chemical Co.), diglycidyl ether of cyclohexanedimethanol (e.g., HELOXY Modifier 107™ from Shell Chemical Co.), trimethylol ethane triglycidyl ether (e.g., HELOXY Modifier 44™ from Shell Chemical Co.), trimethylol propane triglycidyl ether (e.g., HELOXY Modifier 48™ from Shell Chemical Co.), polyglycidyl ether of an aliphatic polyol (e.g., HELOXY Modifier 84™ from Shell Chemical Co.), polyglycol diepoxide (e.g., HELOXY Modifier 32™ from Shell Chemical Co.), diglycidyl ether of bisphenol F (e.g., Araldite™ GY-281™ from Ciba-Geigy Corp.), and 9,9-bis[4-(2,3-epoxypropoxy-phenyl]fluorenone (e.g., Epon 1079™ from Shell Chemical Co.).

Still other epoxy resins contain copolymers of acrylic acid esters or glycidol such as glycidylacrylate and glycidylmethacrylate with one or more copolymerizable vinyl compounds. Examples of such copolymers are 1:1 styrene glycidylmethacrylate, 1:1 methyl methacrylate-glycidylacrylate and a 62.5:24:13.5 methyl methacrylate-ethyl acrylate-glycidylmethacrylate.

Other useful epoxy resins are well known and contain such epoxides as epichlorohydrin; alkylene oxides, such as propylene oxide, styrene oxide, and/or butadiene oxide; and glycidyl esters, such as ethyl glycidate.

The polymers of the epoxy resin can optionally contain other functionalities that do not substantially interfere with cationic polymerization at room temperature. Blends of various epoxy-containing materials are also contemplated. Examples of such blends include two or more weight average molecular weight distributions of epoxy-containing compounds, such as low molecular weight (below 200), intermediate molecular weight (about 200 to 10,000), and higher molecular weight (above about 10,000). Alternatively or additionally, the epoxy resin may contain a blend of epoxy-containing materials having different chemical natures, such as aliphatic and aromatic, or functionalities, such as polar and non-polar.

Epoxy resins that preferably are used as the cationically polymerizable resin include diglycidyl ether of bisphenol F obtained from Ciba Geigy under the tradename Araldite™ GY 281; diglycidyl ether of bisphenol A obtained from Shell Chemical Co. under the tradename Epon 825; 3',4'-epoxycyclohexanemethyl-3,4-epoxycyclohexane carboxylate obtained from Union Carbide under the tradename Cyracure™ UVR 6105; trimethyol propane triglycidyl ether obtained from Shell Chemical Co. under the tradename Heloxy 48; butanediol diglycidyl ether obtained from Ciba Geigy under the tradename RD 2; and bis(3,4-epoxycyclohexylmethyl)adipate obtained from Union Carbide under the tradename ERL 4299. The preferred epoxy resins for providing physical strength and integrity to the cured adhesive composition are made of diepoxide monomers.

Vinyl ethers that may be used as the cationically polymerizable resin include, but are not limited to, tri(ethylene glycol)divinyl ether (TEGDVE), glycidyl vinyl ether (GVE), butanediol vinyl ether (BDVE), di(ethylene glycol) divinyl ether (DEGDVE), 1,4-cyclohexanedimethanol divinyl ether (CHDMDVE), 4-(1-propenyloxymethyl)-1,3-dioxolan-2-one (POMDO), 2-cloroethyl vinyl ether (CEVE), or 2-ethylhexyl vinyl ether (EHVE), ethyl vinyl ether (EVE), n-propyl vinyl ether (NPVE), isopropyl vinyl ether (IPVE), n-butyl vinyl ether (NBVE), isobutyl vinyl ether (IBVE), octadecyl vinyl ether (ODVE), cyclohexyl vinyl ether (CVE), butanediol divinyl ether (BDDVE), hydroxybutyl vinyl ether (HBVE), cyclohexanedimethanol monovinyl ether (CHMVE), tert-butyl vinyl ether (TBVE), tert-amyl vinyl ether (TAVE), dodecyl vinyl ether (DDVE), ethylene glycol divinyl ether (EGDVE), ethylene glycol monovinyl ether (EGMVE), hexanediol divinyl ether (HDDVE), hexanediol monovinyl ether (HDMVE), diethylene glycol monovinyl ether (MVE-2), triethyleneglycol methyl vinyl ether (MTGVE), tetraethylene glycol divinyl ether (DVE-4), trimethylolpropane trivinyl ether (TMPTVE), aminopropyl vinyl ether (APVE), poly-tetrahydrofuran divinyl ether (PTHFDVE), pluriol-E200 divinyl ether (PEG200-DVE), n-butyl vinyl ether (n-BVE), 4-hydroxybutylvinylether (HBVE), ethylene glycol butyl vinyl ether (EGBVE), 2-diethylaminoethyl vinyl ether (DEAEVE), dipropylene glycol divinyl ether (DPGDVE), octadecyl vinyl ether (ODVE), a vinyl ether terminated aromatic ester monomer, a vinyl ether terminated aliphatic ester monomer, a vinyl ether terminated aliphatic urethane oligomer, and a vinyl ether terminated aromatic urethane oligomer.

The acidic components that are used in making the adhesive composition of the present invention are compounds having acidic or acidogenic functional groups that also have adhesion properties. An acidogenic group is a group that can generate an acid, such as an anhydride or an acid halide. Any of four classes of acidic components or combinations thereof may be used in making the adhesive composition of the present invention. Preferably, the acidic component is a compound that also contains a reactive olefinic moiety.

The first class of acidic components is maleic anhydride and its ring-opened derivatives that have at least one acid or acidogenic functionality. The following structures show ring-opened derivatives resulting from the reaction product of maleic anhydride with an alcohol or a primary or secondary amine to form an ester or an amide, as shown below:

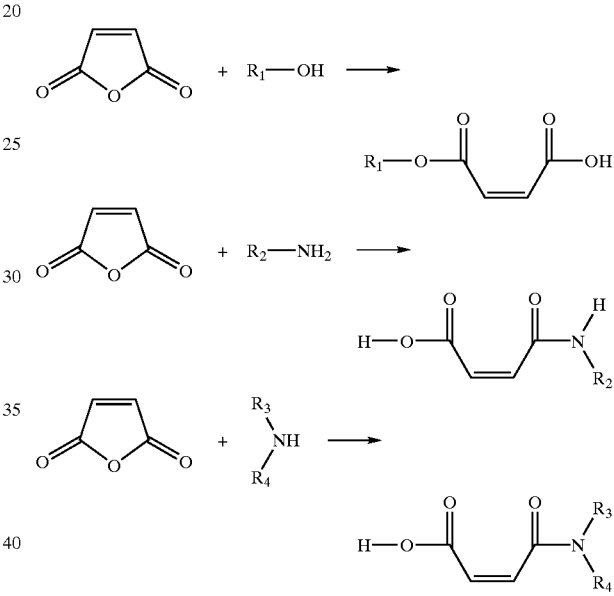

wherein $R_1$, $R_2$, $R_3$, and $R_4$ are independently selected from any aliphatic or aromatic radical. As the basicity of $R_1$, $R_2$, $R_3$, or $R_4$ increases, the rate of cationic polymerization, using one of the reaction products shown above as the acidic component, slows down. A substituent on the acidic component that slows down the rate of cationic polymerization may be chosen to control the reaction rate. However, the selection of a substituent so basic that it stops the polymerization reaction should be avoided. If $R_1$, $R_2$, $R_3$, or $R_4$ is an aliphatic or aromatic radical, then preferably it is an organic radical containing a free radically polymerizable group. Most preferably, the free radically polymerizable group is (meth)acrylate. Examples of suitable components in this class are maleic acid, maleic anhydride, 2-(methacryloyloxy)ethyl maleate (MAEM), and the reaction products of maleic anhydride and 2-hydroxyethylacrylate, 2-hydroxyethylmethacrylate (HEMA), 2- and 3-hydroxypropylacrylate and methacrylate, 1,3- and 2,3-dihydroxypropylacrylate and methacrylate, 2-hydroxypropyl-1,3-diacrylate and dimethacrylate, 3-hydroxypropyl-1,2diacrylate and dimethylacrylate, pentaerythritol diacrylate and dimethacrylate, 2-aminoethylacrylate, 2-aminoethylmethacrylate, 2- and 3-aminopropylacrylate and methacrylate, 1,3- and 2,3- diaminopropylacrylate and methacrylate, 2-aminopropyl-1,3-diacrylate and dimethacrylate, and 3-aminopropyl-1,2-diacrylate and dimethylacrylate. These reaction products have the structures of the compounds shown above.

The second class of acidic components is polymeric polycarboxylic acids of the formula:

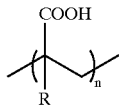

wherein each R is independently selected from H, $CH_3$, or $CH_2CO_2H$ and n can be any integer so long as the acid is at least partially soluble in the other components of the adhesive composition sufficient so as to provide enhanced adhesion. This second class of acidic components also includes copolymers that include the polycarboxylic acid described above and a free radically polymerizable group. Preferably, the acid has a number average molecular weight that is less than about 10,000. More preferably, the number average molecular weight is less than about 5,000. Even more preferably, the number average molecular weight is less than about 3,000. Examples of suitable components in this class are homopolymers and copolymers of acrylic acid (AA), methacrylic acid, and itaconic acid (IA). If poly(acrylic acid) is used, preferably, it has a molecular weight of about 2,500.

The third class of acidic components is compounds of the formula:

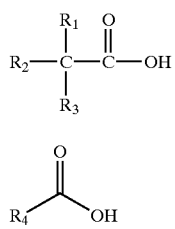

wherein each $R_1$, $R_2$, and $R_3$ of compound (1) and $R_4$ of compound (2) are independently selected from any aliphatic or aromatic radical that does not interfere with cationic polymerization. At least two of the substituents, RI, $R_2$, and $R_3$ of compound (1), each must contain at least one polymerizable group such as free radically polymerizable groups. One of the substituents of compound (1) can be hydrogen. $R_4$ of compound (2) must contain at least two polymerizable groups. $R_1$, $R_2$, and/or $R_3$ may be (meth)acryloyl substituted polycarboxylic acids. Examples of acids that fall into this third category are tartaric acid or citric acid that has been functionalized with at least two ethylenic functionalities. For example, citric acid may be ethylenically functionalized by substituting with an acryloyl or methacryloyl functionality. These polymerizable groups may be attached directly to the acid containing compound or may be optionally attached through a linking group. Preferred linking groups include substituted or unsubstituted alkyl, alkoxyalkyl, aryl, aryloxyalkyl, alkoxyaryl, aralkyl or alkaryl groups. Particularly preferred linking groups comprise an ester functionality and most particularly preferred linking groups comprise an amide functionality. Most preferably, the radical is alkyl or dialkyl aminoethyl (meth)acrylate or hydroxyethyl (meth)acrylate. These are compounds having an acidic group and two unsaturated groups per molecule. An example of a suitable acidic component in this class is 2-({N-[2-(2-methylprop-2-enoyloxy)ethyl]carbamoyloxy}methyl)-3-[N-(2-prop-2-enoyloxyethyl)carbamoyloxy] propanoic acid (PDMA).

The fourth class of acidic components is compounds of the formula:

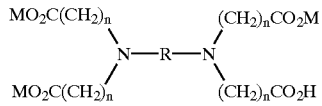

wherein R is an alkyl group having 2 to 4 carbons or a cycloalkyl group having 5 to 6 carbons, each M is independently selected from hydrogen, metal ions, complex organic cations such as tetraalkylanmuonium salts, and alkyl groups, and each n is an integer independently selected from 1 to 4. If M is a metal cation, preferably, it is sodium or potassium. Examples of suitable compounds in this class are ethylenediamine tetraacetic acid (EDTA) and mono-, di-, and tri-salts thereof.

Most preferably, the acidic component is mono-2-(methacryloyloxy)ethyl maleate, maleic anhydride, 2-({N-[2-(2-Methylprop-2-enoyloxy)ethyl]carbamoyloxy}methyl)-3-[N-(2-prop-2-enoyloxyethyl)carbamoyloxy] propanoic acid (PDMA), poly(acrylic acid), ethylenediamine tetraacetic acid, and/or mono-, di-, and tri-salts of ethylenediamine tetraacetic acid. Most preferably, the poly(acrylic acid) has a molecular weight of about 2000. The structures of some of these preferred acidic components are shown below:

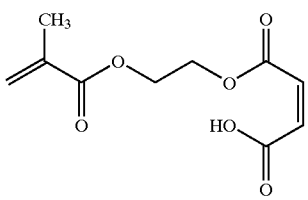

mono-2-(methacryloyloxy)ethyl maleate

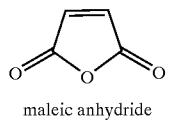

maleic anhydride

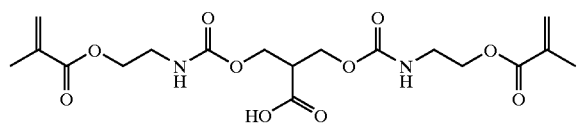

PDMA

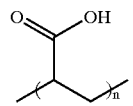

poly(acrylic acid)

A cationic initiator must be used in the composition of the present invention. Free radical initiators may also be used if a free radically polymerizable component is optionally included in the composition. The adhesive composition of the present invention can be photocured or chemically cured. The broad class of cationic initiators available in the industry, such as photoactive cationic nuclei, photoactive cationic moieties, and photoactive cationic organic compounds may be used in the composition of the present invention for photocuring. Cationic intiators such as HCl, HBr, HI, C$_6$H$_5$SO$_3$H, HSbF$_6$, HAsF$_6$, HBF$_4$, or Lewis acids, such as metal halide salts, may be used for chemically curing. Preferably, the adhesive composition of the present invention is photocured. More preferably, the initiator used in the adhesive composition of the present invention includes a diaryliodonium salt. If the initiator only includes a diaryliodonium salt, the adhesive must be cured with UV light. Preferably, the initiator also includes a photosensitizer so that the adhesive composition can be cured using visible light.

Most preferably, the initiator used in forming the polymerizable compositions of the presevt invention is a ternary system that includes a diaryliodonium salt, a sensitizer, and an electron donor compound. This system can function as a cationic and free radical initiator. This ternary photoinitiator system allows efficient cationic polymerization under conditions of room temperature and standard pressure, which permits its use with a variety of photopolymerizable compositions. Use of this ternary initiator system can provide a substantial reduction in the time required for the present compositions to cure to a tack-free gel or solid compared with systems that only contain a diaryliodonium salt and a photosensitizer. This reduction in gel time can in some cases represent about a 30 to 70% decrease in the time required for a resin composition to harden to a tack-free gel or solid. Still further, some compositions fail to polymerize altogether in the absence of an electron donor.

The first component of the preferred ternary photoinitiator system is an iodonium salt (PI), i.e., a diaryliodonium salt. The iodonium salt should be soluble in a monomer used to make the composition and preferably is shelf-stable, meaning it does not spontaneously promote polymerization when dissolved therein in the presence of the sensitizer and the electron donor compound, the second and third components of the preferred photoinitiator system. Accordingly, selection of a particular iodonium salt may depend to some extent upon the particular monomer, sensitizer and donor chosen. Suitable iodonium salts are described in U.S. Pat. Nos. 3,729,313; 3,741,769; 3,808,006; 4,250,053 and 4,394,403. The iodonium salt can be a simple salt, containing an anion such as Cl—, Br—, I— or C$_6$H$_5$SO$_3$—; or a metal complex salt containing an antimonate, arsenate, phosphate orborate such as SbF$_5$OH— or AsF$_6$—. Mixtures of iodonium salts can be used if desired.

Aromatic jodonium complex salts of the structure below may be used as one of the components of the ternary photoinitiator system:

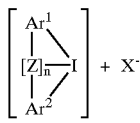

wherein

Ar$^1$ and Ar$^2$ are aromatic groups having 4 to 20 carbon atoms and are selected from the group consisting of phenyl, thienyl, furanyl and pyrazolyl groups;

Z is selected from the group consisting of oxygen; sulfur;

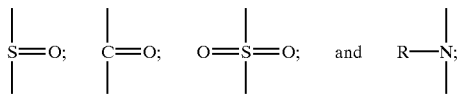

wherein R is aryl (of 6 to 20 carbons, such as phenyl) or acyl (of 2 to 20 carbons, such as acetyl, benzoyl, and the like); a carbon-to-carbon bond; or

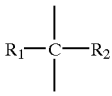

wherein R$_1$ and R$_2$ are selected from hydrogen, alkyl radicals of 1 to 4 carbons, and alkenyl radicals of 2 to 4 carbons;

n is zero or 1; and

X is a halogen-containing complex anion selected from the group consisting of tetrafluoroborate, hexafluorophosphate, hexafluoroarsenate, and hexafluoro anti monate.

The aromatic iodonium cations are stable and are well known and recognized in the art. See for example, U.S. Pat. Nos. 3,565,906; 3,712,920; 3,759,989; and 3,763,187; F. Beringer, et al., Diaryliodonium Salts IX, J. Am. Chem. Soc. 81,342–51 (1959) and F. Beringer, et al., Diaryliodonium Salts XXIII, J. Chem. Soc. 1964, 442–51; F. Beringer, et al., lodonium Salts Containing Heterocyclic Iodine, J. Org. Chem. 30, 1141–8 (1965); J. Crivello et al., Photoinitiated Cationic Polymerization with Triarylsulfonium Salts, J. Polymer Science, 17, 977 (1979).

Representative Ar$^1$ and Ar$^2$ groups are aromatic groups having 4 to 20 carbon atoms selected from phenyl, thienyl, furanyl, and pyrazolyl groups. These aromatic groups may optionally have one or more fused benzo rings (e.g., naphthyl and the like; benzothienyl; dibenzothienyl; benzofuranyl, dibenzofuranyl; and the like). Such aromatic groups may also be substituted, if desired, by one or more of the following non-basic groups which are essentially non-reactive with epoxide and hydroxy: halogen, nitro, N-arylanilino groups, ester groups (e.g., alkoxycarbonyl such as methoxycarbonyl and ethoxycarbonyl, phenoxycarbonyl), sulfo ester groups (e.g., alkoxylsulfonyl such as methoxysulfonyl and butoxysulfonyl, phenoxysulfonyl, and the like), amido groups (e.g., acetamido, butyramido, ethylsulfonamido, and the like), carbamyl groups (e.g., carbamyl, N-alkylcarbamyl, N-phenylcarbamyl, and the like), sulfamyl groups (e.g., sulfamyl, N-alkylsulfamyl, N,N-dialkylsulfamyl, N-phenylsulfamyl, and the like), alkoxy groups (e.g., methoxy, ethoxy, butoxy, and the like), aryl groups (e.g., phenyl), alkyl groups (e.g., methyl, ethyl, butyl, and the like), aryloxy groups (e.g., phenoxy)alkylsulfonyl (e.g., methylsulfonyl, ethylsulfonyl, and the like), arylsulfonyl groups (e.g., phenylsulfonyl groups), perfluoroalkyl groups (e.g., trifluoromethyl, perfluoroethyl, and the like), and perfluoroalkylsulfonyl groups (e.g., trifluoromethylsulfonyl, perfluorobutylsulfonyl, and the like).

Examples of useful aromatic iodonium complex salt photoinitiators include: diphenyliodonium tetrafluoroborate; di(4-methylphenyl)iodoniuti tetrafluoroborate; phenyl-4-methlphenyliodonium tetrafluoroborate; di(4-heptylphenyl)iodonium tetrafluoroborate; di(3-nitrophenyl)iodonium hexafluorophosphate; di(4-chlorophenyl)iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; dinphenyliodonium hexafluoroarsenate; di(4-phenoxyphenyl)iodonium tetrafluoroborate; phenyl-2-thienyliodonium hexafluorophosphate; 3,5-dimethylpyrazolyl-4- phenyliodonium hexafluorophosphate; diphenyliodonium hex afluoroantimonate; 2,2'-diphenyliodonium tetrafluoroborate; di(2,4-dichlorophenyl)iodonium hexafluorophosphate; di(4-bioniophenyl)iodonium hexafluorophosphate; di(4-methoxyphenyl)iodonium hextafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; (4-octyloxyphenyl)phenyliodonium hexafluoroantimonate (OPIA) obtained from GE Silicones, 479–2092C; diphenyliodonium hexafluoroantimonate (DPISbF$_6$); [4-(2-hydroxytetradecyloxyphenyl)]phenyliodonium hexafluoroantimonate (CD 1012) obtained from Sartomer SarCat CD-1012; and [4-(1-methylethyl)phenyl] (4-methylphenyl) iodonium tetrakis (pentafluorophenyl)borate(1−) (RHO 2074) obtained from Rhodia, Inc., Rhodorsil Photoinitiator 2074.

Of the aromatic iodonium complex salts which are suitable for use in the compositions of the invention, diaryliodonium hexafluorophosphate and diaryliodonium hexafluoroantimonate are among the preferred salts. Specific examples of such salts are (4-octyloxyphenyl) phenyliodonium hexafluoroantimonate (OPIA), [4-(2-hydroxytetradecyloxyphenyl)]phenyliodonium hexafluoroantimonate, and [4-(1-methylethyl)phenyl] (4-methylphenyl)iodonium tetrakis (pentafluorophenyl) borate(1−). These salts are preferred because, in general, they are more thermally stable, promote faster reaction, and are more soluble in inert organic solvents than are other aromatic iodonium salts of complex ions.

The second component in the preferred ternary photoinitiator system is the photosensitizer (PS). Desirably, the photoinitiator should be sensitized to the visible spectrum to allow the polymerization to be initiated at room temperature using visible light. The sensitizer should be soluble in the photopolymerizable composition, free of functionalities that would substantially interfere with the cationic curing process, and capable of light absorption within the range of wavelengths between about 300 and about 1000 nanometers.

A sensitizer is selected based in part upon shelf stability considerations. Accordingly, selection of a particular sensitizer may depend to some extent upon the particular adhesive components, iodonium salt, and electron donor chosen.

Suitable sensitizers include one or more compounds in the following categories: ketones, courmarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones, p-substituted aminostyryl ketone compounds, are preferred sensitizers. For applications requiring deep cure (e.g., cure of highly-filled composites), it is preferred to employ sensitizers having an extinction coefficient below about 1000 lmole$^{-1}$ cm$^{-1}$, more preferably about or below 100 lmol$^{-1}$ cm$^{-1}$, at the desired wavelength of irradiation for photopolymerization, or alternatively, the initiator should exhibit a decrease in absorptivity upon light exposure. Many of the alpha-diketones (alpha-dicarbonyl compounds) are an example of a class of sensitizers having this property, and are particularly preferred for dental applications.

By way of example, a preferred class of ketone sensitizers has the formula:

$$ACO(X)_bB$$

where X is CO or CR$^1$R$^2$ where R$^1$ and R$^2$ can be the same or different, and can be hydrogen, alkyl, alkaryl or aralkyl, b is zero or one, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones ofthe above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable α-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzyl, 2,2'- 3,3'- and 4,4'-dihydroxylbenzyl, furyl, di-3,3'-indolylethanedione, 2,3-bomanedione (camphorquinone), biacetyl, 1,2-cyclohexanedione, 1,2-naphthaquinone, acenaphthaquinone, and the like.

Examples of particularly preferred visible light sensitizers include (+/−) camphorquinone (CQ), 97%, Aldrich 12, 489-3; 2-chlorothioxanthen-9-one, Aldrich C7, 240-4; glyoxal; biacetyl; 3,3,6,6-tetramethylcyclohexanedi one; 3,3,7,7-tetramethyl-1,2-cycloheptanedione; 3,3,8,8-tetramethyl-1,2-cyclooctanedione; 3,3,18,18-tetramethyl-1,2-cyclooctadecanedione; dipivaloyl; benzyl; furyl; hydroxybenzyl; 2,3-butanedione; 2,3-pentanedione; 2,3-hexanedione; 3,4-hexanedione; 2,3-heptanedione; 3,4-heptanedione; 2,3-octanedione; 4,5-octanedione; and 1,2-cyclohexanedione. Most preferably, the photosensitizer is (+/−) camphorquinone.

The third component of the preferred photoinitiator system is one or more electron donor compounds (ED). These electron donor compounds act as reaction accelerators and accelerate the photopolymerization rate of adhesive composition. The electron donor compound(s) should meet the requirements set forth below and be soluble in the polymerizable composition. The donor can also be selected in consideration of other factors, such as shelf stability and the nature of the polymerizable materials, iodonium salt and sensitizer chosen. A class of donor compounds that may be useful in the inventive systems may be selected from some of the donors described in Palazzotto et al., U.S. Pat. No. 5,545,676. Possible donor compounds that meet the criteria set forth by Palazzotto et al. must then be tested using one or both of the methods set forth below to determine if they will be useful donors for the adhesive compositions of the present invention.

The donor is typically an alkyl aromatic polyether or an alkyl, aryl amino compound wherein the aryl group is optionally substituted by one or more electron withdrawing groups. Examples of suitable electron withdrawing groups include carboxylic acid, carboxylic acid ester, ketone, aldehyde, sulfonic acid, sulfonate and nitrile groups.

The suitability of a compound for use as an electron donor in the compositions of the invention may be determined by measuring the photoinduced potential of a sample photoinitiator system that includes the compound. The photoinduced potential can be evaluated in the following .O manner. A standard solution is prepared that contains $2.9 \times 10^{-5}$ moles/g of diphenyl iodonium hexafluoroantimonate and $1.5 \times 10^{-5}$ moles/g of camphorquinone (CQ) in 2-butanone. A pH electrode is then immersed in the solution and a pH meter is calibrated to zero mV. A test solution of the standard solution and the compound is prepared next using the compound at a concentration of $2.9 \times 10^{-5}$ moles/g. This test solution is irradiated using blue light having a wavelength of about 400 to 500 nm having an intensity of about 200 to 400 mW/cm$^2$ for about 5 to 10 seconds at a distance of about 1 mm. Millivolts relative to the standard solution are then determined by immersing the pH electrode in the test solution and obtaining a mV reading on the pH meter. Useful donors are those compounds that provide a reading of at least 50 mV relative to the standard solution. Higher mV readings are generally indicative of greater activity.

In some instances there may be some uncertainty regarding the outcome of the above procedure. This may be due to questions or uncertainty arising from the instrumentation employed, from the way the procedure was carried out, or other factors, or one may wish to verify the suitability of a particular compound. A second test may be performed to verify the result obtained by following the above procedure and resolve any such uncertainty.

The second method involves the evaluation of the photoinduced potential of an initiator system that includes the compound compared to a system that includes N,N-dimethylaniline. For this method, a standard solution of $2.9 \times 10^{-5}$ moles/g diphenyl iodonium hexafluoroantimonate, $1.5 \times 10^{-5}$ moles/g camphorquinone (CQ) and $2.9 \times 10^{-5}$ moles/g of N,N-dimethylaniline in 2-butanone is prepared. A pH electrode is then immersed in the solution and a pH meter is calibrated to zero mV. The standard solution is irradiated with blue light having a wavelength of between about 400–500 nm and an intensity of about 200 to 400 mW/cm$^2$ for about 5 to 10 seconds using a focused light source such as a dental curing light at a distance of about 1 mm. After light exposure, the potential of the solution is measured by immersing a pH electrode in the irradiated standard solution and reading the potential in mV using a pH meter. A test solution is then prepared using $2.9 \times 10^{-5}$ moles/g of diphenyl iodonium hexafluoroantimonate, $1.5 \times 10^{-5}$ moles/g of camphorquinone and $2.9 \times 10^{-5}$ moles/g of the compound in 2-butanone. The test solution is irradiated and the photoinduced potential measured using the same technique as described for the standard solution. If the test solution has a photoinduced potential that is the same as or greater than that of the N,N-dimethylaniline containing standard solution, then the compound is a useful donor.

A preferred group of alkyl, aryl amine donor compounds is described by the following structural formula:

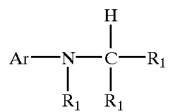

wherein
each $R_1$ is independently H; $C_{1-8}$ alkyl that is optionally substituted by one or more halogen, —CN, —OH, —SH, $C_{1-18}$ alkoxy, $C_{3-18}$ alkylthio, $C_{3-18}$ cycloalkyl, aryl, COOH, COOC$_{1-18}$ alkyl, (C$_{1-18}$ alkyl)$_{0-1}$—CO—C$_{1-18}$ alkyl SO$_3$R$^2$; aryl that is optionally substituted by one or more electron withdrawing groups; or the R$^1$ groups together may form a ring, where R$^2$ is H; C$_{1-18}$ alkyl that is optionally substituted by one or more halogen, —CN, —OH, —SH, C$_{1-18}$ akoxy, C$_{1-18}$ alkylthio, C$_{3-18}$ cycloalkyl, aryl, COOH, COOC$_{1-18}$ alkyl, (C$_{1-18}$ alkyl)$_{0-1}$—CO—C$_{1-18}$ alkyl, or SO$_3$H; and Ar is aryl that is optionally substituted by one or more electron withdrawing groups. Suitable electron withdrawing groups include —COOH, —COOR$^2$, —SO$_3$R$^2$, —CN, —CO—C$_{1-18}$ alkyl, and C(O)H groups.

A preferred group of aryl alkyl polyethers has the following structural formula:

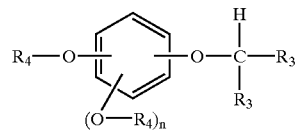

wherein n=1–3, each R$_3$ is independently H or C$_{1-18}$ alkyl that is optionally substituted by one or more halogen, —CN, —OH, —SH, C$_{1-18}$ alkoxy, C$_{1-18}$ alkylthio, C$_{3-8}$ cycloalkyl, aryl, substituted aryl, —COOH, —COOC$_{1-18}$ alkyl, —(C$_{1-18}$ alkyl)$_{0-1}$—COH, —(C$_{1-18}$ alkyl)$_{0-1}$—CO-C$_{1-18}$ alkyl, —CO—C$_{1-18}$ alkyl, —C(O)H or —C$_{2-8}$ alkenyl groups and each R$_4$ can be C$_{1-18}$ alkyl that is optionally substituted by one or more halogen, —CN, —OH, —SH, C$_{1-18}$ alkoxy, C$_{1-18}$ alkylthio, C$_{3-18}$ cycloalkyl, aryl, substituted aryl, —COOH, —COOC$_{1-18}$ alkyl, —(C$_{1-18}$ alkyl)$_{0-1}$—COH, —(C$_{1-18}$ alkyl)$_{0-1}$—CO—C$_{1-18}$ alkyl, —CO—C$_{1-18}$ alkyl, —C(O)H or —C$_{2-18}$ alkenyl groups.

In each of the above formulas, the alkyl groups can be straight-chain or branched, and the cycloalkyl group preferably has 3 to 6 ring carbon atoms but may have additional alkyl substitutions up to the specified number of carbon atoms. The aryl groups may be carbocyclic or heterocyclic aryl, but are preferably carbocyclic, and more preferably are phenyl rings.

Preferred donor compounds include, but are not limited to, 4,4'-bis(diethylamino)benzophenone (BDEAB), 99+%, Acros 17081–0250; 4-dimethylaminobenzoic acid (4-DMABA); ethyl p-dimethylaminobenzoate (EDMAB), 99+%, Acros 11840–1000; 3-dimethylamino benzoic acid (3-DMABA); 4-dimethylaminobenzoin (DMAB); 4-dimethylaminobenzaldehyde (DMABAL); 1,2,4-trimethoxybenzene (TMB); and N-phenylglycine (NPG).

The compounds of the ternary photoinitiator system are provided in an amount effective to initiate or enhance the rate of cure of the resin system. It has been found that the amount of donor that is used can be critical, particularly when the donor is an amine. Too much donor can be deleterious to cure properties. Preferably, the sensitizer is present in about 0.05–5 weight percent based on resin compounds of the overall composition. More preferably, the sensitizer is present at about 0.10–1.0 weight percent. Similarly, the iodonium initiator is preferably present at about 0.05–10.0 weight percent, more preferably at about 0.10–5.0 weight percent, and most preferably at about 0.50–4.0 weight percent. Likewise, the donor is preferably present at about 0.01–5.0 weight percent.

An alternative photoinitiator system for cationic polymerization includes the use of organometallic complex cations essentially free of metal hydride ormetal alkyl functionality selected from those described in U.S. Pat. No. 4,985,340, and such description is incorporated herein by reference and has the formula:

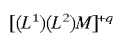

wherein
M represents a metal selected from the group consisting of Cr, Mo, W, Mn, Re, Fe, Ru, Os, Co, Rh, Ir, Pd, Pt and Ni, preferably Cr, Mo, W, Mn, Fe, Ru, Co, Pd, and Ni; and most preferably Mn and Fe;

$L^1$ represents 1 or 2 cyclic, polyunsaturated ligands that can be the same or different ligand selected from the group consisting of substituted and unsubstituted cyclopentadienyl, cyclohexadienyl, and cycloheptatrienyl, cycloheptatriene, cyclooctatetraene, heterocyclic compounds and aromatic compounds selected from substituted or unsubstituted arene compounds and compounds having 2 to 4 fused rings, and units of polymers, e.g., a phenyl group of polystyrene, poly(styrene-co-butadiene), poly(styrene-co-methyl methacrylate), poly(a-methylstyrene), and the like; a cyclopentadiene group of poly(vinylcyclopentadiene); a pyridine group of poly(vinylpyridine), and the like, each capable of contributing 3 to 8 electrons to the valance shell of M;

$L^2$ represents none, or 1 to 3 nonanionic ligands contributing an even number of electrons that can be the same or different ligand selected from the group of carbon monoxide, ketones, olefins, ethers, nitrosonium, phosphines, phosphites, and related derivatives of arsenic and antimony, organoitriles, amines, alkynes, isonitriles, dinitrogen, with the proviso that the total electronic charge contributed to M results in a net residual positive charge of q to the complex;

q is an integer having a value of 1 or 2, the residual charge of the complex cation.

Organometallic salts are known in the art and can be prepared as described in, for example, EPO No. 094,914 and U.S. Pat. Nos. 5,089,536, 4,868,288, and 5,073,476, and such descriptions are incorporated herein by reference.

Examples of preferred cations include:
bis($\eta^5$-cyclopentadienyl)iron(1+), bis($\eta^5$-methylcyclopentadienyl)iron (1+), ($\eta^5$-cyclopentadienyl)($\eta^5$-methylcyclopentadienyl)iron (1+), and bis($\eta^5$-trimethylsilylcyclopentadienyl)iron (1+);

bis($\eta^6$-xylenes)iron(2+), bis($\eta^6$-mesitylene)iron(2+), bis ($\eta^6$-durene)iron(2+), bis($\eta^6$-pentamethylbenzene)iron(2+), and bis($\eta^6$-dodecylbenzene)iron(2+);

($\eta^5$-cyclopentadienyl)($\eta^6$-xylenes)iron(1+), commonly abbreviated as (CpFeXy)(1+), $\eta^5$-cyclopentadienyl)($\eta^6$-toluene)iron(1+), $\eta^5$-cyclopentadienyl)($\eta^6$-mesitylene)iron(1+), $\eta^5$-cyclopentadienyl)($\eta^6$-pyrene)iron(1+), $\eta^5$-cyclopentadienyl)($\eta^6$-naphthalene)iron(1+), and $\eta^5$-cyclopentadienyl)($\eta^6$-dodecylphenyl)iron(1+).

Still further, a variety of visible or near-IR photoinitiators may be used for photopolymerization of free-radically polymerizable materials in the composition of the present invention. Free-radical initiators useful in the invention, e.g., those that are photochemically active in the wavelength region of greater than 400 to 1200 nm, may include the ternary initiator system discussed above and the class of acylphosphine oxides, as described in European Patent Application No. 173567. Tertiary amine reducing agents may be used in combination with an acylphosphine oxide. Illustrative tertiary amines useful in the invention include ethyl 4-(N,N-dimethylamino)benzoate and N,N-dimethylaminoethyl methacrylate. The initiator can be employed in catalytically-effecitve amounts, such as from about 0.1 to about 5 weight percent, based on the weight of ethylenically-unsaturated compound present, of the acylphosphine oxide plus from about 0.1 to about 5 weight percent, based on the weight of ethylenically-unsaturated compound present, of the tertiary amine.

Commercially-available phosphine oxide photoinitiators capable of free-radical initiation when irradiated at wavelengths ofgreater than 400 nm to 1200 nm include a 25:75 mixture, by weight, of bis(2,6-dimethoxybenzoyl)-2,4,4-trimethylpentyl phosphine oxide and 2-hydroxy-2methyl-1phenylpropan-1-one(IRGACURE™ 1700, Ciba Specialty Chemicals),2-benzyl-2-(N,N-dimethylamino)-1-(4-morpholinophenyl)-1-butanone (IRGACURE™ 369, Ciba Specialty Chemicals), bis($\eta^5$-2,4-cyclopentadien-1-yl)-bis (2,6-difluoro-3-(1H-pyrrol-1-yl)phenyl)titanium (IRGACURE™ 784 DC, Ciba Specialty Chemicals), a 1:1 mixture, by weight, of bis(2,4,6-trimnethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRN™ LR8893X, BASF Corp., Charlotte, N.C.). Preferably, initiators such as Bisphenol A glycidyl methacrylate (BisGMA) and tributyl boron oxide (TBBO) are used to polymerize any free radically polymerizable materials included in the composition of the present invention.

Free-radical initiators useful in the invention, e.g., those that are photochemically active in the wavelength region of greater than 400 to 1200 nm, also may include the class of ionic dye—counterion complex initiators comprising a borate anion and a complementary cationic dye. Borate anions useful in these photoinitiators generally can be of the formula

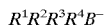

wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodaminel and azomethine dyes. Specific examples of useful cationic dyes include Methylene Blue, Safranine O, and Malachite Green. Quaternary ammonium groups useful as counterions can be trimethylcetylammonium, cetylpyridinium, and tetramethylammonium. Other organophilic cations can include pyridinum, phosphonium, and sulfonium. Photosensitive transition metal cordination complexes that may be used include complexes of cobalt, ruthenium, osmium, zinc, iron, and iridum with ligands such as pyridine, 2,2' -bipyridine, 4,4'-dimethyl-2,2'-bipyridine, 1,10-phenanthroline, 3,4,7,8-tetramethylphenanthroline, 2,4,6-tri(2-pyridyl-s-triazine) and related ligands.

As discussed previously, a polyol may be added to the adhesive composition of the present invention as an optional component. Polyols that may be added include, but are not limited to poly(tetrahydrofuran) (PTHF) (preferably, average M=ca. 250, Aldrich 34, 526-1) and 2-oxepanone (polymer with 2-ethyl-2-(hydroxymethyl)-1,3-propane diol) obtained from Union Carbide under the tradename Tone 301. The preferred polyol for extending the gel-state during the photocure of the fonnulation is poly(tetrahydrofuran).

Optionally, an epoxy/polyol blend may be added to the adhesive composition in place of or in addition to the epoxy resin or other cationically polymerizable resin used in formulating the adhesive composition. Epoxy/polyol blends that may be added include, but are not limited to, Blend 4216-G: 42% GY281 and 42% UVR-6105 and 16% PTHF, Blend 4216-E: 42% Epon 825 and 42% UVR 6105 and 16% PTHF, Blend 4804-G: 48% GY 281 and 48% UVR 6105 and 4% PTHF, Blend 4804-E: 48% Epon 825 and 48% UVR 6105 and 4% PTHF, Blend 5000-G: 50% UVR 6105 and 50% GY 281, and Blend 5000-E: 50% UVR 6105 and 50% Epon 825.

As also discussed previously, a free radically polymerizable component may be added to the adhesive composition. This is a material having free radically active functional groups. A free radically active functional group refers to a chemical moiety that is activated in the presence of an initiator capable of initiating free radical polymerization such that it is available for reaction with other compounds bearing free radically active functional groups. The free radically polymerizable component can be made of monomers, oligomers, and polymers having one or more ethylenically unsaturated groups. Suitable materials contain at least one ethylenically unsaturated bond, and are capable of undergoing addition polymerization.

Suitable free radically-polymerizable monomers may contain at least one ethylenically-unsaturated bond, can be oligomers or polymers, and are capable of undergoing addition polymerization. Such monomers include mono-, di- or poly- acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1-4-cyclohexanedio diacryl ate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, tris(hydroxyethylisocyanurate)trimethacrylate; the bisacrylates and bis-methacrylates ofpolyethylene glycols of molecular weight 200–500, copolymterizable mixtures of acrylated monomers such as those of U.S. Pat. No. 4,652, 274, incorporated herein by reference, and acrylated oligomers such as those of U.S. Pat. No. 4,642,126, incorporated herein by reference; unsaturated amides such as methylene bis-acrylamide, methylene bis-methacrylamide, 1,6-hexamethylene bisacrylamide, diethylene triamine tris-acrylamide and beta-methacrylaminoethyl methacrylate; and vinyl compounds such as styrene, diallyl phthalate, divinyl succinate, divinyl adipate and divinylphthalate. Mixtures of two or more monomers can be used if desired. Preferably, the free radically polymerizable material used is mono-, di-, or poly-acrylates and methacrylates such as methyl acrylate, methyl methacryle, ethyl acrylate, glycidyl methacrylate, 2-isocyanatoethyl methacrylate, limonene oxide, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclhexanediol diacrylate, penterythritol triacrylate, pentaerythritol tetracrylate, pentaerythritol tetramethacrylate, sorbitol hexacrylate, bis[1-929acryloxy)]-p-ethosyphenyl dimethylmethane, bis[1-(3-acryloxy-2-hydroxy)}-p-propoxyphenyldimethylmethane, and trihydroxyethyl-isocyanurate trimethacrylate; the bisacrylates and bis-methacryles of polyethylene glycols of molecular weight 200–500, copolymerizable mixtures of acrylated monomers such as those in U.S. Pat. No. 4,652, 274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

As also discussed previously, a compound with a reactive olefinic moiety may also be included in the adhesive formulation. This reactive olefinic moiety may be located on the acidic component or may be a separate compound. Some of the preferred acidic components listed above include reactive olefinic moieties thereon.

Still further, this composition may include multifunctional compounds that contain several of the functional groups discussed above combined in the same molecule. For example, a compound may contain cationically and free radically polymerizable groups in the same molecule. This composition may also include combinations of each of the components discussed above.

The adhesive composition of the present invention should include about 10–99 wt % cationically polymerizable component, about 0.1–30 wt % acidic component, and about 0.1–10 wt % of the initiator that is capable of initiating cationic polymerizaiton. All percentages of components throughout this application are weight percentages unless otherwise noted. It also may contain up to about 90% of the optional free radically polymerizable component, up to about 20% of a polyol, and up to about 90% compounds containing olefinic moieties other than acidic components containing olefinic moieties. Preferably, the adhesive composition includes about 75% cationically polymerizable component, about 20% acidic component, and about 5% initiator capable of initiating cationic polymerization.

Preferred formulations of the adhesive compositions of the present invention include those listed in Examples 4, 7, 11, 14, 18, 22, 24, 26, 30, 32, 34, 36, 38, 40, 41, 42, 44, 46, 49, 52 and 54. Most preferably, the adhesive compositions of the present invention are the formulations disclosed in Examples 24, 49, 52 or 54. The percentages of components discussed infra do not account for the amount of initiator in the formulation. The first of these most preferred formulations includes 45.6% Epon 825,45.6% UVR 6105,3.8% pTHF, and 5.0% maleic anhydride. The second of these most preferred formulations includes 38.4% Epon 825, 38.4% UVR 6105, 3.2% pTHF, and 20.0% MAEM. The third ofthese most preferred formulations includes 26.88% Epon 825,26.88% UVR 6105, 2.24% pTHF, 24.0% HEMA, and 20.0% MAEM. The fourth of these most preferred formulations includes 38.4% UVR 6105, 38.4% GY 281, 3.2% Heloxy 48, and 20.0% MAEM.

The adhesive composition of the present invention can be adhered to any hard tissue. It is especially useful in dental formulations for adhesive bonding of cationically polymerizable dental restorative materials to dentin and enamel substrates. Still further, it is able to bond to dental metals, ceramics, and composites. It is also useful as a dental material for sealing cracks and fissures in tooth structures and in cationically curable tooth restorative materials. This adhesive is a cationically initiated adhesive which is compatible with a cationically photoinitiated dental restorative system and is capable of bonding the dental restorative to the tooth substrate. Preferably, it has a bond strength to hard tissue of at least about 10 kg/cm$^2$.

The adhesive composition of the present invention is applied in the form of a relatively thin layer to a hard tissue surface. Examples of hard tissue surfaces include teeth (the component parts of which are enamel, dentin, and cementum), bone, fingernails, and hoofs. Prior to application of the adhesive composition, the hard tissue surface may be pre-treated or primed to enhance adhesion to the hard tissue surface (e.g., using an acid etchant, primer, and/or adhesion promoter).

Following application to the hard tissue surface the adhesive composition is preferably polymerized to form an adhesive layer on the hard tissue surface. Polymerization takes place by exposing the adhesive composition to polymerizable conditions sufficient to form a hardened composition adhered to the hard tissue. Preferably, polymerization is effected by exposing the adhesive composition to a radiation source, preferably, a visible light source. Suitable visible light sources include a Visilux™ dental curing light commercially available from 3M Company of St. Paul, Minn. Such lights have an intensity of about 200–700 mW/cm$^2$ at a wavelength of 400–500 nm.

Following polymerization to form the cured adhesive, a second composition may be applied to the adhesive. The adhesive compositions are particularly useful for bonding dental compositions, especially where the dental composition contains cationically active functional groups such as epoxy groups or vinyl ether groups. The dental compositions may be filled or unfilled, and include dental materials such as direct esthetic restorative materials (e.g., anterior and posterior restoratives), prostheses, sealants, veneers, cavity liners, crown and bridge cements, artificial crowns, artificial teeth, dentures, and the like. In the case of dental compositions containing cationically active functional groups, the dental composition is polymerized via a cationic mechanism following application to the bonding adhesive composition of the present invention.

In an alternate embodiment of the present invention, additional acidic component is applied to the hard tissue before the adhesive composition is applied to the hard tissue. The acidic component may be applied as a neat liquid, in a concentrated solution, or with a solvent, such as acetone, ethanol or HEMA. In still another alternative embodiment, the adhesive composition is formed on the substrate by first applying an acidic component to the substrate, subsequently applying a cationically polymerizable component and corresponding initiator, and then curing these layers.

The term "composite" as used herein refers to a filled dental material. The term "restorative" as used herein refers to a composite which is polymerized after it is disposed adjacent to a tooth. The term "prosthesis" as used herein refers to a composite which is shaped and polymerized for its final use (e.g., as crown, bridge, veneer, inlay, onlay, or the like) before it is disposed adjacent to a tooth. The term "sealant" as used herein refers to a lightly filled composite or to an unfilled dental material which is polymerized after it is disposed adjacent to a tooth. "Polymerizable" refers to curing or hardening the dental material, e.g., by cationic or cationic and free-radical mixed reaction mechanisms.

The advantage of the adhesive composition of the present invention is that it demonstrates enhanced composite-to-tooth substrate bonding levels compared to corresponding formulations not containing an acidic component. The compositions of the present invention enable a cationically rich or even cationically pure system to cure to a solid mass. This composition is able to cationically cure at the interface of a tooth's surface. The acidic components used in the adhesive composition of the present invention enhance the bonding of cationic restoratives to tooth substrates by undergoing physicochemical interactions with hard tissue. The adhesive compositions of the present invention successfully polymerize on the surface of hard tissue to bond with the hard tissue, yet at the same time, can successfully bond to compositions that include cationically active groups. In one embodiment of the present invention, after the adhesive composition is applied to the hard tissue and exposed to polymerization conditions, a second polymerizable composition comprising a cationically active functional group and a polymerization initiator capable of initiating cationic polymerization is applied, and it is exposed to polymerization conditions to form a hardened composition adhered to the hard tissue.

Another embodiment of the present invention is a dental restorative material that is comprised of a cationically polymerizable component, an acidic component, an initiator capable of initiating cationic polymerization such as the ternary photoinitiator discussed above, and a dental filler that does not substantially interfere with cationic polymerization in an amount of between about 10 to 90% by weight based on the total weight of the dental restorative material.

A further embodiment of the present invention is a kit comprising the adhesive composition of the present invention and an instruction sheet for the application of the adhesive composition to hard tissue. Preferably, the kit also includes a dental material capable of bonding to the adhesive. Preferably, the dental material is a dental metal, a ceramic, a composite, or a dental restorative material that comprises a mixture of a cationically polymerizable component, an acidic component, an initiator capable of initiating cationic polymerization, and a dental filler that does not substantially interfere with cationic polymerization in an amount of between about 10 to 90% by weight based on the total weight of the dental restorative material. The kit may further include one or more pre-treatment materials selected from the group consisting of etchants, primers, adhesion promoters, and combinations thereof.

The following examples show properties of adhesive compositions of the present invention. The percentages of components discussed in these examples does not account for the amount of initiator in the formulation. These examples are to be construed as illustrative and not in a limiting sense. Unless otherwise indicated, all parts and percentages are by weight, and all molecular weights are weight average molecular weight.

EXAMPLES USING TEST A

Adhesive formulations containing different acidic components were prepared, photocured and evaluated. They were applied to abraded, etched dentin and enamel substrates, and evaluated using Test A, a cure, bond and interface test.

The technique of Test A consisted of the following eleven steps using cross-sectioned molar test specimens: (1) abrade and etch; (2) rinse and blot dry; (3) apply pretreatment(s) if used; (4) apply adhesive; (5) irradiate for 60 seconds at 2 mm; (6) let stand 10 minutes; (7) evaluate usin dental explorer; (8) rate degree of cure=0, 1 or 2; (9) rate quality of adhesive/substrate bond=0, 1, or 2; (10) rate quality of adhesive/substrate interface=0, 1 or 2; (11) overall adhesive performance=sum of ratings for steps 8, 9 and 10.

Test A rating scheme is summarized in the following chart:

Test A Rating Scheme

| Parameters Rated | Rating/Description | | |
|---|---|---|---|
| | 0 | 1 | 2 |
| Adhesive Cure | not cured to slightly cured; fluid | partially cured; rubbery, viscoelastic | well cured; hard |
| Adhesive/Substrate Bond | adhesive layer easy to remove | adhesive layer removable with some effort | adhesive layer difficult to remove |
| Adhesive/Substrate Interface | residual uncured adhesive layer that is fluid | residual partially cured adhesive layer, wherein the residual layer is gel-like | no residual liquid adhesive layer |

Test A is a subjective test and therefore is most useful as a preliminary screening test to determine components that are most likely to provide good curing and adhesive characteristics. While the overall trends of the data from Test A show that the addition of an acidic component helps the curing and adhesive properties of the composition, there are specific instances where the data does not show this trend. This can be explained because of the qualitative nature of the test and thus increased variability in results, the fact that the structure and composition of human dentin and enamel varies from person to person and with location in the tooth, and the fact that the photoinitiator system has not yet been optimized for the best cure and bonding.

The Test A performance ratings of seven adhesives (Example Nos. 1–7) on abraded and etched dentin substrates are shown in Table I. Epoxy/maleate formulations (Example Nos. 3, 4, 5, and 7) generally exhibited better performance (overall ratings of 3 to 5) than epoxy formulations without maleate (Example Nos. 1 and 6; overall ratings of 1 and 2 respectively) Examples 1 and 6 do not contain acidic components and are not formulations of the present invention but were tested for comparison. Example 1 is for comparison against Examples 2–5, and Example 6 is for comparison against Example 7. The maleate in Examples 2–5 and 7 is the acidic component of the formulation. The test results for Examples 2–5 show that the acidic component must be present in a sufficient quantity for adhesion.

The Test A performance ratings of seven adhesive compositions (Example Nos. 8–14) on abraded and etched dentin and enamel are presented in Table II. Examples containing maleate (Nos. 9, 11, 13, and 14) had better overall ratings (5, 6, 5, and 6 respectively on dentin) than Examples 8, 10, and 12 (overall ratings of 2, 2, and 0 respectively on dentin) which did not contain maleate. Results on enamel were mixed, and not as dramatic. Example Nos. 12, 13, and 14 contained HEMA in addition to epoxy/polyol blend 4804E. Examples 8, 10, and 12 do not contain acidic components and are not formulations of the present invention but were tested for comparison. Example 8 is for comparison against Example 9, Example 10 is for comparison against Example 11, and Example 12 is for comparison against Examples 13–14. The maleate in Examples 9, 11, and 13–14 is the acidic component of the formulation.

The Test A performance ratings of eight adhesive compositions (Example Nos. 15–22) on abraded and etched dentin substrates are shown in Table III. These formulations contained no polyol. Maleate improved the overall ratings (from 3 to 5 or 6) for formulations containing epoxy blends with Heloxy 48 (compare Examples 17 and 18; 21 and 22). Examples 15, 17, 19, and 21 do not contain acidic components and are not formulations of the present invention but were tested for comparison. Example 15 is for comparison against Example 16, Example 17 is for comparison against Example 18, Example 19 is for comparison against Example 20, and Example 21 is for comparison against Example 22. The maleate in Examples 16, 18, 20, and 22 is the acidic component of the formulation.

EXAMPLES 1–7

TABLE I

Test A-Cure, Bond, Interface; Abrade and Etch Only
(Adhesive Formulations Containing MAEM)

| Example No. | Adhesive Composition | Overall Rating on Dentin |
|---|---|---|
| 1 | 4216G 100 wt % | 1 |
| 2 | 90% 4216G and 10% 2-(methacryloyloxy)ethyl maleate | 0 |
| 3 | 80% 4216G and 20% 2-(methacryloyloxy)ethyl maleate | 3 |
| 4 | 75% 4216G and 25% 2-(methacryloyloxy)ethyl maleate | 4 |
| 5 | 70% 4216G and 30% 2-(methacryloyloxy)ethyl maleate | 3 |
| 6 | 4216E 100 wt % | 2 |
| 7 | 80% 4216E and 20% 2-(methacryloyloxy)ethyl maleate | 5 |

*All adhesive compositions in Examples 1–7 contained 3.0% CD1012 and 2.0% CQ and 0.05% EDMAB.

EXAMPLES 8–14

TABLE II

Test A-Cure, Bond, Interface Test; Abrade and Etch Only
(Adhesive Formulations Containing MAEM or MAEM/HEMA Mixtures)

| Example No. | Adhesive Composition | Overall Rating on Dentin (D); Enamel (E) |
|---|---|---|
| 8 | 4804E 100 wt % (1.5% CD1012 and 2.0% CQ and 0.05% EDMAB) | 2 (D); 5 (E) |
| 9 | 95% 4804E and 5% 2-(Methacryloyloxy) ethyl maleate (1.5% CD1012 and 2.0% CQ and 0.05% EDMAB) | 5 (D); 3 (E) |
| 10 | 4804E 100 wt % | 2 (D); 2 (E) |
| 11 | 80% 4804E and 20% 2-(methacryloyloxy) ethyl maleate | 6 (D); 6 (E) |
| 12 | 70% 4804E and 30% HEMA | 0 (D); 5 (E) |
| 13 | 95% [70% 4804E and 30% HEMA] and 5% 2-(Methacryloyloxy)ethyl maleate | 5 (D); 4 (E) |
| 14 | 80% [70% 4804E and 30% HEMA] and 20% 2-(Methacryloyloxy)ethyl maleate | 6 (D); 6 (E) |

*All adhesive compositions in Examples 8–14 contained 3.0% CD1012 and 2.0% CQ and 0.05% EDMAB unless indicated.

EXAMPLES 15–22

TABLE III

Test A-Cure, Bond, Interface; Abrade and Etch Only
(Adhesive Formulations Containing MAEM with and without Heloxy 48)

| Example No. | Adhesive Composition | Overall Rating on Dentin |
|---|---|---|
| 15 | 5000G 100 wt % | 4 |
| 16 | 80% 5000G and 20% 2-(Methacryloylxy)ethyl maleate | 3 |
| 17 | 96% 5000G and 4% Heloxy 48 | 3 |
| 18 | 80% [96% 5000G and 4% Heloxy 48] and 20% 2-(Methacryloyloxy)ethyl maleate | 6 |
| 19 | 5000E 100 wt % | 3 |
| 20 | 80% 5000E and 20% 2-(Methacryloyloxy)ethyl maleate | 4 |
| 21 | 96% 5000E and 4% Heloxy 48 | 3 |
| 22 | 80% [96% 5000E and 4% Heloxy 48] and 20% 2-(Methacryloyloxy)ethyl maleate | 5 |

*All adhesive compositions in Examples 15–22 contained 3.0% CD1012 and 2.0% CQ and 0.05% EDMAB.

TABLE IV

Test A-Cure, Bond, Interface Test; Abrade and Etch Only
(Adhesive Formulations Containing Maleic Anhydride or PDMA with and without HEMA)

| Example No. | Adhesive Composition | Overall Rating on Dentin (D); Enamel (E) |
|---|---|---|
| 23 | 4804E 100 wt % | 4 (D); 4(E) |
| 24 | 95% 4804E and 5% Maleic anhydride | 6 (D); 6 (E) |
| 25 | 70% 4804E and 30% HEMA | 0 (D); 5 (E) |
| 26 | 95% [70% 4804E and 30% HEMA] and 5% Maleic anhydride | 5 (D); 6 (E) |
| 27 | 90% [70% 4804E and 30% HEMA] and 10% Maleic anhydride | 3 (D); 6 (E) |
| 28 | 80% [70% 4804E and 30% HEMA] and 20% Maleic anhydride | 3 (D); 5 (E) |
| 29 | 82.4% 4804E and 17.6% HEMA | 2 (D); 5 (E) |
| 30 | 70% 4804E and 15% HEMA and 15% PDMA | 6 (D); 6 (E) |

*All adhesive compositions in Examples 23–30 contained 3.0% CD1012 and 2.0% CQ and 0.05% EDMAB.

EXAMPLES 23–30

The Test A performance ratings of eight adhesive compositions (Example Nos. 23–30) on abraded/etched dentin and enamel are presented in Table IV. On dentin, examples containing maleic anhydride (Nos. 24, 26, 27, 28) had superior overall ratings when compared to respective mixes without maleic anhydride (Nos. 23 and 25), with the examples containing 5% maleic anhydride (Nos. 24 and 26) having the highest overall ratings, 6 and 5 respectively. Example No. 30, which contained PDMA, had a markedly higher overall rating (6) than Example No.29 (overall rating=2) which did not contain PDMA. Generally, the same trends were noted on enamel.

Examples 23, 25, and 29 do not contain acidic components and are not formulations of the present invention but were tested for comparison. Example 23 is for comparison against Example 24, Example 25 is for comparison against Example 26–28, and Example 29 is for comparison against Example 30. The maleic anhydride in Examples 24 and 26–28 is the acidic component of these formulations, and PDMA in Example 30 is the acidic component of this formulation.

EXAMPLES 31–41

The Test A performance ratings of 11 adhesive/pretreatment systems (Example Nos. 31–41) on abraded/etched dentin and enamel are presented in Table V. For systems using Pretreatment "a" (Example Nos. 31–38), adhesive formulations containing maleic anhydride (Example Nos. 32, 33, and 38) had higher overall ratings than respective adhesive formulations not containing an acidic component (Example Nos. 31 and 37). Adhesive formulations containing maleate (Examples 34 and 36) had higher overall ratings than a respective formulation not containing an acidic component (Example No.31). Still further, adhesive formulations containing PDMA (Examples Nos. 35 and 36) had higher overall ratings than a respective fornmulation not containing an acidic component (Example No. 31). Example No. 32 (20% maleic anhydride) had a higher overall rating (6) than Example No. 33 (3) which contained 5 wt % maleic anhydride. The same trends can be noted on enamel. For systems using Pretreatment "b", Example Nos. 40 (containing maleic anhydride and 41 (containing maleate) had higher overall ratings (6) on both dentin and enamel, than did Example No. 39 which contained no acidic component.

Examples 31, 37, and 39 do not contain acidic components and are not formulations of the present invention but were tested for comparison. Example 31 is for comparison against Examples 32–36, Example 37 is for comparison against Example 38, and Example 39 is for comparison against Examples 40–41. The maleic anhydride in Examples 32–33, 38, and 40 is the acidic component of these formulations. The maleate in Examples 34 and 41 is the acidic component of these formulations. The PDMA in Examples 35–36 is the acidic component of these formulations.

TABLE V

Test A-Cure, Bond, Interface Test-Abrade and Etch with
Pretreatments: (a) Scotch Bond Multi-Purpose ™ (SBMP) Activator/Primer
available from 3M; (b) SBMP Activator
(Adhesive Formulations Containing Selected Additives)

| Example No. | Adhesive Composition and Pretreatment (a or b) | Overall Rating on Dentin (D); Enamel (E) |
|---|---|---|
| 31 | 70% 4804E and 30% HEMA (a) | 2 (D); 2 (E) |
| 32 | 80% [70% 4804E and 30% HEMA] and 20% Maleic anhydride (a) | 6 (D); 6 (E) |
| 33 | 95% [70% 4804E and 30% HEMA] and 5% Maleic anhydride (a) | 3 (D); 6 (E) |
| 34 | 80% [70% 4804E and 30% HEMA] and 20% 2-(Methacryloyloxy)ethyl maleate (a) | 6 (D); 6 (E) |
| 35 | 70% 4804E and 15% HEMA and 15% PDMA (a) | 4 (D); 3 (E) |
| 36 | 80% [70% 4804E and 15% HEMA and 15% PDMA] and 20% 2-(Methacryloyloxy)ethyl maleate (a) | 5 (D); 4 (E) |
| 37 | 4804E 100 wt % (a) | 2 (D); 3 (E) |
| 38 | 95% 4804E and 5% Maleic anhydride (a) | 5 (D); 6 (E) |
| 39 | 70% 4804E and 30% HEMA (b) | 2 (D); 3 (E) |
| 40 | 80% [70% 4804E and 30% HEMA] and 20% Maleic anhydride (b) | 6 (D); 6 (E) |
| 41 | 80% [70% 4804E and 30% HEMA] and 20% 2-(Methacryloyloxy)ethyl maleate (b) | 6 (D); 6 (E) |

*All adhesive compositions in Examples 31–41 contained 3.0% CD1012 and 2.0% CQ and 0.05% EDMAB.

EXAMPLES 42–47

Further tests using Test A were conducted using EDTA as the acidic component. Example 45 shows a formulation with no acidic component. Examples 43 and 47 show an ethyl maleate acidic component being used. Examples 42, 44, and 46 had the highest ratings, and the compositions of these examples included EDTA and ethyl maleate as the acidic components.

TABLE VI

Test A-Cure, Bond, Interface Test; Abrade and Etch Only
(Adhesive Formulations Containing MAEM and EDTA, NA$_2$)

| Example No. | Adhesive No. | Overall Rating on Dentin (D); Enamel (E) |
|---|---|---|
| 42 | 80% [99.5% [500G-Heloxy48(96-4 w %)]- 0.5% EDTA] and 20% [2-(methacryloyloyx)ethyl maleate] | 6 (D); 6 (E) |
| 43 | 80% [5000G-Heloxy48(96-4 w %)] and 20% [2-(methacryloyloxy)ethyl maleate] | 4 (D); 6 (E) |
| 44 | 99.5% 4804E and 0.5% EDTA, Na$_2$ | 6 (D); 6 (E) |
| 45 | 4804E 100 wt % | 2 (D); 2 (E) |
| 46 | 79.5% 4804E and 0.5% EDTA, Na$_2$ and 20% [2-(methacryloyloxy)ethyl maleate] | 6 (D); 6 (E) |
| 47 | 80% 4804E and 20% [2-(methacryloyloxy)ethyl maleate] | 4 (D); 6 (E) |

*All adhesive compositions in Examples 54–59 contained 3.0% CD1012 and 2.0% CQ and 0.05% EDMAB.

EXAMPLES USING TEST B

These examples represent the result of Test B, shear bond strength tests performed using experimental adhesive formulations to bond (a) composite to composite, (b) composite to dentin substrate, and (c) composite to enamel substrate.

The composite used in the Test B shear bond strength test consisted of 16.5 wt. % cationically polymerizable resin and 83.5 wt. % silane treated filler. Specifically, the resin contained 41.47 wt. % Araldite GY281 epoxy monomer (Ciba Geigy Inc.), 41.47 wt. % Cyracure UVR6105 epoxy monomer (Union Carbide Inc.), 15.21 wt. % polytetrahydrofuran (M.W. 250) Aldrich Chemical Company), 0.50 wt. % camphorquinone (Eastman Kodak Inc.), 1.25 wt. % Sarcat CD1012 (Sartomer Inc.), and 0.10 wt. % ethyl-4-dimethylaminobenzoate (Aldrich). The filler consisted of a 96 to 4 weight ratio of quartz (average particle size ofapproximately 5 microns) and Cab-O-Sil M5 fumed silica (Cabot Corp.). The filler was silane treated with 5 wt. % glycidoxypropyltrimethoxysilane (G6720 from United Chemical Technologies).

Composite-to-Composite: Epoxy-based dental composite was placed in the 7 mm×2.5 mm cylindrical cavity of a clear acrylic mold. The mold was vibrated slightly to smooth the surface of the composite. A thin layer of adhesive formulation was applied and irradiated for 60 seconds @2 mm with a Visilux™ dental light gun (can be obtained from 3M). A flexible circular mold (3.1 mm I.D.) was applied to the center of the adhesive coated substrate, and filled in two increments with epoxy-based composite. Each increment was irradiated for.60 sec. The mold was inverted, and the composite irradiated through the 11 mm thick bottom of the clear mold. Samples were stored for 24 hr at 37° C. prior to shear bond strength testing as described below for composite-to-tooth substrate tests.

Composite-to-Dentin or -Enamel: The test procedure for the shear bond strength determinations was as follows. The teeth used in this test were nonerupted, human third molars without visible physical defects. To prepare dentin substrates, the teeth were mounted in a methacrylate block and sectioned through the crown perpendicular to the long axis with a low speed diamond saw to expose a dentin surface. Tooth substrates were then abraded with 320 grit carborundum paper, rinsed with water and blotted dry with a tissue. To prepare enamel substrates, teeth were sectioned longitudinally into equal halves. A proper section of the crown enamel was chosen and abraded with 320 grit paper to make a flat surface. Teeth were then appropriately mounted in methacrylate blocks. Substrates were etched with an aqueous solution of 38% phosphoric acid for 15 seconds, rinsed with water, and dried with an air syringe. The adhesive was applied liberally to the entire test surface and irradiated with a dental lamp for 60 seconds at 2 mm. After 5 minutes, a teflon rmold, 3.5 nun in diameter, was applied to the surface into which an epoxy-based dental composite material, was placed and cured with a dental light gun in approximately 1.5 mm increments to build up a composite button approximately 4 mm in height. The teeth were then stored in deionized water at body temperature, 37° C., for 24 hours before conducting the bond strength tests. The bond strength measurements were conducted with a model 1125 Instron mechanical test machine. The embedded teeth were held by gripping the methacrylate block and the load applied with a chisel-shaped device at a crosshead speed of 0.5 mm/min. The maximum load required to fracture the sample divided by the bonded area was recorded as the shear bond strength.

EXAMPLES 48–59

The Test B shear bond strength performance evaluations for twelve adhesive compositions (Example Nos. 48–59) are given in Table VII. For examples 48–50, formulations containing acidic components (No. 49, maleate or No. 50, maleic anhydride) had measurable shear bond strengths to dentin of 34.7 kg/cm$^2$ and 8.7 kg/cm$^2$ respectively, whereas the example without acidic component (No. 48 demonstrated no measurable bond strength. On enamel the bond strength of No. 48 (5.4 kg/cm$^2$) was increased over 15-fold by the addition of maleate to the formulation (Example No. 49; 78.4 (kg/cm$^2$)). The bond strength to dentin of the adhesive containing HEMA in Example No. 51 (0.31 kg/cm$^2$) was markedly improved by the addition of 20% maleate (12.3 kg/cm$^2$; Example No. 52). For examples 53–55, formulations with no polyol containing acidic components (No. 54, maleate or No. 55, maleic anhydride) had measurable shear bond strengths to dentin of 43.9 kg/m$^2$ and 1.8 kg/cm$^2$ respectively, whereas the example without acidic component (No. 53) demonstrated no measurable bond strength. On enamel, the formulation which did not contain the maleate additive (Example No. 53) had a shear bond strength value of 9.3 kg/cm$^2$ whereas the formulation with the maleate (Example No. 54) had a measured shear bond strength of 104.4 kg/cm$^2$, a 10-fold increase. The formulation containing acidic component PDMA also resulted in a measurable bond strength (1.4 kg/cm$^2$, No. 57) as compared to Example No. 56 which contained no PDMA. On enamel, Example No. 59 containing poly(acrylic acid) had markedly improved bond strength, 42.9 kg/cm$^2$ vs. 8.0 kg/cm$^2$ kg/cm$^2$, as compared to Example No. 58 which did not contain the acidic component. Composite-to-composite bond strength results for selected examples demonstrate the ability of the adhesive to form a bond with experimental epoxy-based composites.

Examples 48, 51, 53, 56, and 58 do not contain acidic components and are not formulations of the present invention but were tested for comparison. Example 48 is for comparison against Examples 49–50, Example 51 is for comparison against Example 52, Examples 53 is for comparison against Example 54–55, Example 56 is for comparison against Example 57, and Example 58 is for comparison against Example 59. The maleate in Examples 49, 52, and 54 is the acidic component of these formulations. The maleic anhydride in Examples 50 and 55 is the acidic component of these formulations. The PDMA in Example 57 is the acidic component of this formulation. The poly(acrylic acid) in Example 59 is the acidic component of this formulation.

TABLE VII

Test B-Shear Bond Strength

| | | Mean Shear Bond Strength kg/cm$^2$ ± S.D. | | |
|---|---|---|---|---|
| Example No. | Adhesive Composition | Composite to Composite | Composite to Abraded, Etched Dentin | Composite to Abraded, Etched Enamel |
| 48 | 4804E 100 wt % | nt | 0 | 5.4 ± 6.4 |
| 49 | 80% 4804E and 20% 2-(Methacryloyloxy)ethyl maleate | 135.8 ± 68.4 | 34.7 ± 26.5 | 78.4 ± 27.8 |
| 50 | 95% 4804E and 5% Maleic anhydride | 201.1 ± 88.8 | 8.7 ± 6.9 | nt |
| 51 | 70% 4804E and 30% HEMA | nt | 0.31 ± 0.31 | nt |
| 52 | 80% [70% 4804E and 30% HEMA] and 20% 2-(Methacryloyloxy)ethyl maleate | 178.6 ± 44.9 | 12.3 ± 17.4 | nt |
| 53 | 96% 5000G and 4% (Heloxy 48) | nt | 0 | 9.3 ± 8.8 |
| 54 | 80% [96% 5000G and 4% Heloxy 48] and 20% 2-(Methacryloyloxy)ethyl maleate | 246.0 ± 65.3 | 43.9 ± 38.8 | 104.2 ± 74.2 |
| 55 | 95% [96% 5000G and 4% Heloxy 48] and 5% Maleic anhydride | nt | 1.8 ± 3.0 | nt |
| 56 | 82.4% 4804E and 17.6% HEMA | nt | 0 | nt |
| 57 | 70% 4804E and 15% HEMA and 15% PDMA | nt | 1.4 ± 1.8 | nt |
| 58 | 4216G 100 wt % (1.144% CD1012 and 0.46% CQ and 0.09% EDMAB) | nt | nt | 8.0 ± 5.7 |

TABLE VII-continued

Test B-Shear Bond Strength

| | | Mean Shear Bond Strength $kg/cm^2$ ± S.D. | | |
|---|---|---|---|---|
| Example No. | Adhesive Composition | Composite to Composite | Composite to Abraded, Etched Dentin | Composite to Abraded, Etched Enamel |
| 59 | 97.2% 4216G and 2.8% poly(acrylic acid) (1.144% CD1012 and 0.46% CQ and 0.09% EDMAB) | 336.0 ± 114.2 | 0 | 42.9 ± 28.6 |

*All tooth substrates were etched with 37 wt % phosphoric acid before testing; nt = no test. To convert values to MPa: $(kg/cm^2)/9.7972$ = MPa.
**All compositions in Examples 42–53 contained 3.0% CD1012 and 2.0% CQ and 0.05% EDMAB except where indicated.

From the foregoing, it will be seen that this invention is one that is well adapted to attain all the ends and objects herein above set forth together with other advantages which are obvious and inherent to the composition. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative and not in a limiting sense.

We claim:

1. An adhesive composition for bonding to hard tissue, comprising:
   (a) a cationically polymerizable component;
   (b) an acidic component comprising one or more compounds having at least one acidic or acidogenic functional group; and
   (c) an initiator capable of initiating cationic polymerization, wherein said adhesive composition is able to bond to hard tissue.

2. The adhesive composition of claim 1, wherein said initiator is a photoinitiator.

3. The adhesive composition of claim 2, wherein said photoinitiator is a photoinitiator system comprising an iodonium salt and a visible light sensitizer.

4. The adhesive composition of claim 3, wherein said system further comprises an electron donor compound, wherein the initiator system has a photoinduced potential greater than or equal to that of N,N-dimethylaniline in a standard solution of $2.9 \times 10^{-5}$ moles/g diphenyl iodonium hexafluoroantimonate and $1.5 \times 10^{-5}$ moles/g camphorquinone in 2-butanone.

5. The adhesive composition of claim 1, wherein said initiator is a chemically curing initiator.

6. The adhesive composition of claim 5, wherein said chemically curing initiator is selected from the group consisting of HCl, HBr, HI, $C_6H_5SO_3H$, $HSbF_6$, $HAsF_6$, $HBF_4$, and Lewis acids.

7. The adhesive composition of claim 1, wherein said acidic component has at least one reactive olefinic moiety.

8. The adhesive composition of claim 1, further comprising:
   a free radically polymerizable component.

9. The adhesive composition of claim 8, further comprising:
   a free radical initiator capable of initiating free radical polymerization.

10. The adhesive composition of claim 1, further comprising:
    a polyol.

11. The adhesive composition of claim 8, further comprising:
    a polyol.

12. The adhesive composition of claim 1, wherein said cationically polymerizable component is selected from the group consisting of epoxy resins, vinyl ethers, oxetanes, spiroorthocarbonates, spiro-orthoesters and combinations thereof.

13. The adhesive composition of claim 1, wherein said hard tissue is selected from the group consisting of enamel, cementum, dentin, fingernails, hoofs, and bone.

14. The adhesive composition of claim 1, wherein said adhesive composition further is able to bond to materials selected from the group consisting of dental metals, ceramics, and composite restoratives.

15. The adhesive composition of claim 1, wherein said composition has a bond strength to hard tissue of at least about 10 $kg/cm^2$.

16. The adhesive composition of claim 1, wherein said composition comprises the mixture of about 10–99 weight % of said cationically polymerizable component, about 0.1–30 weight 0% of said acidic component, and about 0.1–10 weight % of said initiator.

17. An adhesive composition for bonding to hard tissue, comprising a mixture of:
    (a) an epoxide;
    (b) an acidic component comprising one or more compounds having at least one acidic or acidogenic functional group and a reactive olefinic moiety; and
    (c) a photoinitiator capable of initiating cationic polymerization, wherein said adhesive composition is able to bond to hard tissue.

18. The adhesive composition of claim 17, wherein said composition is comprised of diglycidyl ether of Bisphenol A, 3,4-epoxycyclohexylmethyl-3,4-epoxycyclohexene carboxylate, poly(tetrahydrofutran), and (methacrloyloxy) ethyl maleate.

19. The adhesive composition of claim 17, wherein said composition is comprised of 3,4-epoxycyclohexylmethyl-3,4-epoxycyclohexene carboxylate, diglycidyl ether of bisphenol F, trimethylol propane triglycidyl ether, and (methacryloyloxy)ethyl maleate.

20. A method of bonding to a material, comprising:
    (a) providing a material selected from the group consisting of hard tissue, dental metals, ceramics, and composite restoratives;

(b) applying to said material an adhesive composition comprising a mixture of a cationically polymerizable component, an acidic component comprising one or more compounds having at least one acidic or acidogenic functional group, and an initiator capable of initiating cationic polymerization; and (c) exposing said adhesive composition to polymerization conditions to form a hardened composition adhered to said material.

21. The method of claim 20, wherein said exposing step comprises photocuring or chemically curing.

22. The method of claim 21, wherein said exposing step comprises irradiating said adhesive composition with visible light.

23. The method of claim 20, further comprising:
treating said hard tissue prior to application of said composition with an agent selected from the group consisting of etchants, primers, adhesion promoters, and combinations thereof.

24. The method of claim 20, further comprising:
applying an acidic component to said hard tissue before applying said adhesive composition to said hard tissue.

25. The method of claim 20, further comprising:
applying a second polymerizable composition comprising a cationically active functional group and a polymerization initiator capable of initiating cationic polymerization; and
exposing said second composition to polymerization conditions to form a haidened composition adhered to said hard tissue.

26. The method of claim 25, further comprising:
applying an acidic component to said hard tissue before applying said adhesive composition to said hard tissue.

27. A method of bonding to hard tissue, comprising:
(a) applying an acidic component to said hard tissue to form a first layer;
(b) subsequently applying a cationically polymerizable component, an acidic component comprising one or more compounds having at least one acidic or acidogenic functional group and cationic initiator mixture to said hard tissue to form a second layer; and
(c) exposing said first and second layer to polymerization conditions to form a hardened coposition adhered to said hard tissue.

28. A kit, comprising:
an adhesive composition comprising a mixture of a cationically polymerizable component, an acidic component comprising one or more compounds having at least one acidic or acidogeenc functional group, and an initiator capable of initiating cationic polymerization, wherein said adhesive composition forms an adhesive capable of bonding to a hard tissue upon exposure to polymerization conditions; and
an instruction sheet for the application of said adhesive composition to hard tissue.

29. The kit of claim 28, further comprising:
a dental material capable of bonding to said adhesive.

30. The kit of claim 29, wherein said dental material is selected from the group consisting of dental metals, ceramics, composites, and a dental restorative material comprising the mixture of a cationically polymerizable component, an acidic component, an initiator capable of initiating polymerization, and a dental filler that does not substantially interfere with cationic polymerization in an amount of between about 10 to 90% by weight based on the total weight of the dental restorative,material.

31. The kit of claim 30, further comprising:
pretreatment material selected from the group consisting of etchants, primers, adhesion promoters, and combinations thereof.

32. The kit of claim 28, further comprising:
a second polymerizable composition comprising a cationically active functional group and a polymerization initiator capable of initiating cationic polymerization, wherein said second composition forms a hardened composition adhered to said hard tissue upon exposure to polymerizaiton conditions.

33. A material, comprising:
a hard tissue; and
an adhesive composition adhered to said hard tissue, wherein said composition comprises the mixture of a cationically polymerizable component, an acidic component comprising one or more compounds having at least one acidic or acidogenic functional group, and an initiator capable of initiating cationic polymerization.

34. The material of claim 33, wherein said hard tissue is selected from the group consisting of enamel, cementum, dentin, fingernails, hoofs, and bone.

35. An adhesive composition for bonding to hard tissue, comprising:
(a) a cationically polymerizable component;
(b) an acidic component; and
(c) an initiator capable of initiating cationic polymerization,
wherein said adhesive composition is able to bond to hard tissue, and wherein said acidic component is selected from the group consisting of

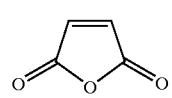
(1)

maleic anhydride;

ring-opened derivatives of maleic anhydride having at least one acid or acidogenic functionality of structure (2), (3) or (4):

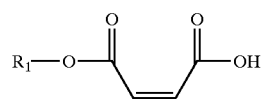
(2)

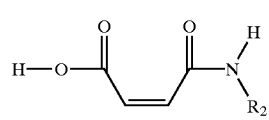
(3)

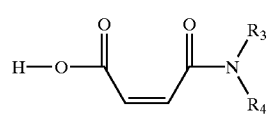
(4)

wherein each $R_1$, $R_2$, $R_3$, and $R_4$ is independently selected from any aliphatic or aromatic radical;

polymeric polycarboxylic acids of the formula:

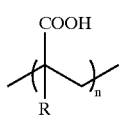
(5)

wherein each R is independently selected from H, CH$_3$, or CH$_2$CO$_2$H, and n is any integer and copolymers that include said polycarboxylic acids so long as said polymeric polycarboxylic acid is at least partially soluble in the other components of the adhesive composition;

a compound of the formula:

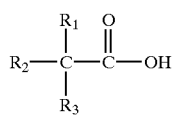
(6)

wherein at least two of R$_1$, R$_2$, and R$_3$ are independently selected from any aliphatic or aromatic radical that has at least one polymerizable group and wherein the resulting compound does not interfere with cationic polymerization;

a compound of the formula:

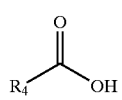
(7)

wherein R$_4$ is any aliphatic or aromatic radical that has at least two polymerizable groups and wherein the resulting compound does not interfere with cationic polymerization;

a compound of the formula:

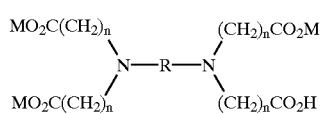
(8)

wherein R is an alkyl group having 2 to 4 carbons or a cycloalkyl group having 5 to 6 carbons, each M is independently selected from hydrogen, metal ions, complex organic cations, and alkyl groups, and each n is an integer independently selected from 1 to 4; and combinations thereof.

36. An adhesive composition for bonding to hard tissue, comprising:
(a) a cationically polymerizable component;
(b) an acidic component comprising a polycarboxylic acid having a number average molecular weight that is less than about 10,000; and
(c) an initiator capable of initiating cationic polymerization, wherein said adhesive composition is able to bond to hard tissue.

37. An adhesive composition for bonding to hard tissue, comprising:
(a) a cationically polymerizable component;
(b) an acidic component selected from the group consisting of maleic acid; maleic anhydride; 2-(methacryloyloxy)ethyl maleate; the reaction products of maleic anhydride and 2-hydroxyethylacrylate, 2-hydroxyethylmethacrylate (HEMA), 2- and 3-hydroxypropylacrylate and methacrylate, 1,3- and 2,3-dihydroxypropylacrylate and methacrylate, 2-hydroxypropyl-1,3-diacrylate and dimethacrylate, 3-hydroxypropyl-1,2diacrylate and dimethylacrylate, pentaerythritol diacrylate and dimethacrylate, 2-aminoethylacrylate, 2-aminoethylmethacrylate, 2- and 3-aminopropylacrylate and methacrylate, 1,3- and 2,3-diaminopropylacrylate and methacrylate, 2-aminopropyl-1,3-diacrylate and dimethacrylate, 3-aminopropyl-1,2diacrylate and dimethylacrylate; homopolymers and copolymers of poly(acrylic acid), polymethacrylic acid, and poly(itaconic acid); 2-({N-[2-(2-methylprop-2-enoyloxy)ethyl]carbamoyloxy}methyl)-3-[N-(2-prop-2-enoyloxyethyl)carbamoyloxy]propanoic acid (PDMA); ethylenediamine tetraacetic acid (EDTA); and mono-, di-, and tri- salts of EDTA; and
(c) an initiator capable of initiating cationic polymerization, wherein said adhesive somposition is able to bond to hard tissue.

38. An adhesive composition for bonding to hard tissue, comprising a mixture of:
(a) a cationically polymerizable component;
(b) an acidic component; and
(c) an initiator capable of initiating cationic polymerization, wherein said adhesive composition is able to bond to hard tissue with a bond strength of at least about 10 kg/cm$^2$, and wherein said acidic component is selected from the group consisting of

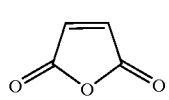
(1)

maleic anhydride;

ring-opened derivatives of maleic anhydride having at least one acid or acidogenic functionality of structure (2), (3) or (4):

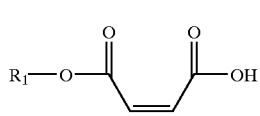
(2)

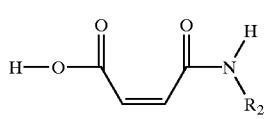
(3)

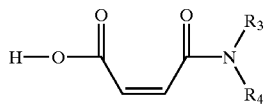
(4)

wherein each R$_1$, R$_2$, R$_3$, and R$_4$ is independently selected from any aliphatic or aromatic radical;

polymeric polycarboxylic acids of the formula:

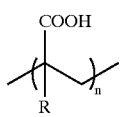
(5)

wherein each R is independently selected from H, CH$_3$, or CH$_2$CO$_2$H, and n is any integer and copolymers that include said polycarboxylic acids so long as said polymeric polycarboxylic acid is at least partially soluble in the other components of the adhesive composition;

a compound of the formula:

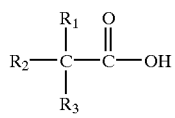
(6)

wherein at least two of R$_1$, R$_2$, and R$_3$ are independently selected from any aliphatic or aromatic radical that has at least one polyrnerizable group and wherein the resulting compound does not interfere with cationic polymerization;

a compound of the formula:

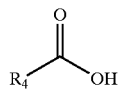
(7)

wherein R$_4$ is any aliphatic or aromatic radical that has at least two polymerizable groups and wherein the resulting compound does not interfere with cationic polymerization;

a compound of the formula:

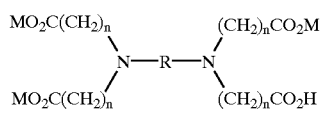
(8)

wherein R is an alkyl group having 2 to 4 carbons or a cycloalkyl group having 5 to 6 carbons, each M is independently selected from hydrogen, metal ions, complex organic cations, and alkyl groups, and each n is an integer independently selected from 1 to 4; and combinations thereof.

39. An adhesive composition for bonding to hard tissue, comprising a mixture of:
(a) acationically polymerizable component present in an amountof about 10–99% by weight of the total weight of the mixture;
(b) an acidic component present in an amount of about 0.1–30% by weight of the total weight of the mixture and comprising maleic anhydride or one or more of ring-opened derivatives of maleic anhydride having at least one acid or acidogenic functionality of structure (2), (3) or (4):

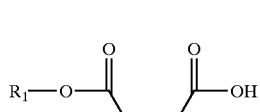
(2)

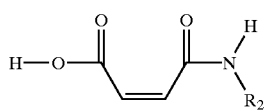
(3)

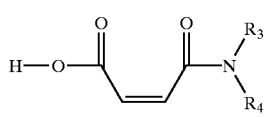
(4)

wherein each R$_1$, R$_2$, R$_3$ and R$_4$ is independently selected from any aliphatic or aromatic radical; and
(c) an initiator capable of initiating cationic polymerization and present in an amount of about 0.1–10% by weight of the total weight of the mixture, wherein said adhesive composition is able to bond to hard tissue with a bond strength of at least about 10 kg/cm$^2$.

40. An adhesive composition for bonding to hard tissue, comprising a mixture of:
(a) a cationically polymerizable component present in an amount of about 10–99% by weight of the total weight of the mixture;
(b) an acidic component present in an amount of about 0.1–30% by weight of the total weight of the mixture and comprising polymeric polycarboxylic acids of the formula:

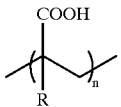

wherein each R is independently selected from H, CH$_3$, or CH$_2$CO$_2$H, and n is any integer and copolymers that include said polycarboxylic acids so long as said polymeric polycarboxylic acid is at least partially soluble in the other components of the adhesive composition; and
(c) an initiator capable of initiating cationic polymerization and present in an amount of about 0.1–10% by weight of the total weight of the mixture, wherein said adhesive composition is able to bond to hard tissue with a bond strength of at least about 10 kg/cm$^2$.

41. An adhesive composition for bonding to hard tissue, comprising a mixture of:
(a) a cationically polymerizable component present in an amount of about 10–99% by weight of the total weight of the mixture;
(b) an acidic component present in an amount of about 0.1–30% by weight of the total weight of the mixture and comprising a compound of the formula:

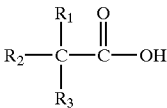

wherein at least two of R$_1$, R$_2$, and R$_3$ are independently selected from any aliphatic or aromatic radical that has at least one polymerizable group and wherein the resulting compound does not interfere with cationic polymerization; and (c) an initiator capable of initiating cationic polymerization and present in an amount of about 0.1–10% by weight of the total weight of the mixture, wherein said adhesive composition is able to bond to hard tissue with a bond strength of at least about 10 kg/cm$^2$.

42. An adhesive composition for bonding to hard tissue, comprising a mixture of:
   (a) a cationically polymerizable component present in an amount of about 10–99% by weight of the total weight of the mixture;
   (b) an acidic component present in an amount of about 0.1–30% by weight of the total weight of the mixture and comprising a compound of the formula:

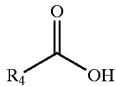

wherein $R_4$ is any aliphatic or aromatic radical that has at least two polymerizable groups and wherein the resulting compound does not interfere with cationic polymerization; and
   (c) an initiator capable of initiating cationic polymerization and present in an amount of about 0.1–10% by weight of the total weight of the mixture, wherein said adhesive composition is able to bond to hard tissue with a bond strength of at least about 10 kg/cm$^2$.

43. An adhesive composition for bonding to hard tissue, comprising a mixture of:
   (a) a cationically polymerizable component present in an amount of about 10–99% by weight of the total weight of the mixture;
   (b) an acidic component present in an amount of about 0.1–30% by weight of the total weight of the mixture and comprising a compound of the formula:

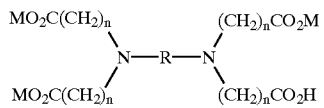

wherein R is an alkyl group having 2 to 4 carbons or a cycloalkyl group having 5 to 6 carbons, each M is independently selected from hydrogen, metal ions, complex organic cations, and alkyl groups, and each n is an integer independently selected from 1 to 4; and (c) an initiator capable of initiating cationic polymerization and present in an amount of about 0.1–10% by weight of the total weight of the mixture, wherein said adhesive composition is able to bond to hard tissue with a bond strength of at least about 10 kg/cm$^2$.

* * * * *

UNITED STATES PATENT AND TRADEMARK OFFICE
CERTIFICATE OF CORRECTION

PATENT NO.    : 6,610,759 B1
DATED         : August 26, 2003
INVENTOR(S)   : Cecil C. Chappelow et al.

It is certified that error appears in the above-identified patent and that said Letters Patent is hereby corrected as shown below:

Column 1,
Line 30, delete "INTVENTION" and insert -- INVENTION -- therefor..
Line 57, delete "TID" between "curable" and "groups".

Column 2,
Line 30, delete "the.same." and insert -- the same --therefor.

Column 3,
Line 1, delete "ofthe" and insert -- of the -- therefor.
Line 34, delete "polymershaving" and insert -- polymers having -- therefor.

Column 4,
Line 5, delete "McGrawv-Hill" and insert -- McGraw-Hill -- therefor.
Line 12, delete "Bisphendl" and insert -- Bisphenol -- therefor.
Line 21, delete "420$^{TM}$" and insert -- 4201$^{TM}$ -- therefor.
Line 30, delete "flamne" and insert -- flame -- therefor.
Line 51, delete "butanedol" and insert -- butanediol -- therefor.

Column 5,
Line 3, delete "l: 1" and insert -- 1:1 -- therefor.
Line 28, delete "epoxycyclohexanemethyl-3,4-epoxycyclohcxane" and insert
-- epoxycyclohexanemethyl-3,4-epoxycyclohexane -- therefor.

Column 6,
Line 6, delete "acidic.or" and insert -- acidic or -- therefore.

Column 7,
Line 26, delete "Ifpoly(acrylic acid)" and insert -- If poly(acrylic acid) -- therefor.
Line 45, delete "RI" and insert -- $R_I$ -- therefor.

Column 9,
Line 3, delete "ofthe" and insert -- of the -- therefor.
Line 42, delete "orborate" and insert -- or borate -- therefor.
Line 46, delete "jodonium" and insert -- iodonium -- therefor.

Column 10,
Line 17, delete "hexafluoro anti monate" and insert -- hexafluoroantimonate -- therefor.
Line 57, delete "di(4-methylphenyl)iodoniuti" and insert -- di(4-methyphenyl)iodonium -- therefor.

UNITED STATES PATENT AND TRADEMARK OFFICE
CERTIFICATE OF CORRECTION

PATENT NO. : 6,610,759 B1
DATED : August 26, 2003
INVENTOR(S) : Cecil C. Chappelow et al.

It is certified that error appears in the above-identified patent and that said Letters Patent is hereby corrected as shown below:

Column 12,
Line 10, delete "ofthe" and insert -- of the -- therefor.

Column 13,
Line 61, delete "$C_{1-8}$" and insert -- $C_{1-18}$ -- therefor.
Line 62, delete "$C_{3-18}$ alkylthio" and insert -- $C_{1-18}$ alkylthio -- therefor.

Column 14,
Line 2, delete "akoxy" and insert -- alkoxy -- therefor.
Line 22, delete "$C_{3-8}$ cycloalkyl" and insert -- $C_{3-18}$ cycloalkyl -- therefor.
Line 25, delete "$C_{2-8}$ alkenyl" and insert -- $C_{2-18}$ alkenyl -- therefor.
Line 63, delete "ormetal" and insert -- or metal -- therefor.

Column 16,
Line 19, delete "LUCIRN$^{TM}$" and insert -- LUCIRIN$^{TM}$ -- therefor.

Column 17,
Line 37, delete "diacryl ate" and insert -- diacrylate -- therefor.

Column 18,
Line 46, delete "825,45.6%" and insert -- 825, 45.6% -- therefor.
Line 50, delete "ofthese" and insert -- of these -- therefor.
Line 51, delete "825,26.88%" and insert -- 825, 26.88% -- therefor.

Column 19,
Line 63, delete "ofthe" and insert -- of the -- therefor.

Column 21,
Line 60, delete "ofthe" and insert -- of the -- therefor.

Column 24,
Line 59, delete "fornmulation" and insert -- formulation -- therefor.

Column 26,
Line 42, delete "ofap-" and insert -- of ap- -- therefor.
Line 56, delete "for.60" and insert -- for 60 -- therefor.

UNITED STATES PATENT AND TRADEMARK OFFICE
CERTIFICATE OF CORRECTION

PATENT NO. : 6,610,759 B1
DATED : August 26, 2003
INVENTOR(S) : Cecil C. Chappelow et al.

It is certified that error appears in the above-identified patent and that said Letters Patent is hereby corrected as shown below:

Column 31,
Line 29, delete "haidened" and insert -- hardened -- therefor.
Line 44, delete "coposition" and insert -- composition -- therefor.
Line 50, delete "acidogeenc" and insert -- acidogenic -- therefor.

Column 35,
Line 59, delete "acationically" and insert -- a cationically -- therefor.
Line 60, delete "amountof" and insert -- amount of -- therefor.

Column 37,
Line 7, delete "cationical ly" and insert -- cationically -- therefor.

Signed and Sealed this

Tenth Day of August, 2004

JON W. DUDAS
*Acting Director of the United States Patent and Trademark Office*